(12) United States Patent
Gibson et al.

(10) Patent No.: US 6,518,282 B1
(45) Date of Patent: Feb. 11, 2003

(54) 4-ARYLPIPERIDINE DERIVATIVES FOR THE TREATMENT OF PRURITUS

(75) Inventors: Stephen Paul Gibson, Kent (GB); Ivan Tommasini, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/576,780

(22) Filed: May 23, 2000

(30) Foreign Application Priority Data

May 28, 1999 (GB) .............................. 9912415

(51) Int. Cl.⁷ ..................... C07D 211/12; A61K 31/445
(52) U.S. Cl. ........................ 514/317; 546/192
(58) Field of Search ............ 514/317; 546/192

(56) References Cited

U.S. PATENT DOCUMENTS

| | | | |
|---|---|---|---|
| 4,081,450 A | 3/1978 | Zimmerman | 546/185 |
| 4,191,771 A | 3/1980 | Zimmerman | 514/317 |
| 5,136,040 A | 8/1992 | Werner | 546/218 |
| 5,364,867 A | 11/1994 | DeHaven-Hudkins et al. | 514/326 |
| 5,498,718 A | 3/1996 | Werner | 546/348 |

FOREIGN PATENT DOCUMENTS

| | | |
|---|---|---|
| DE | 4341403 | 6/1995 |
| EP | 0013078 | 7/1980 |
| EP | 0136863 | 4/1985 |
| EP | 0506468 A1 | 9/1992 |
| EP | 0506478 A1 | 9/1992 |
| EP | 0287339 | 8/1994 |
| EP | 0506468 B1 | 4/1995 |
| EP | 0657428 | 6/1995 |
| EP | 0747357 | 12/1996 |
| EP | 0506478 B1 | 9/1997 |
| EP | 0938898 | 9/1999 |
| GB | 1525584 | 8/1975 |
| GB | 1525584 | 9/1978 |
| GB | 2038812 | 11/1979 |
| WO | 9515327 | 6/1995 |
| WO | 9854136 | 12/1998 |
| WO | 9959971 | 11/1999 |
| WO | 0039089 | 7/2000 |

OTHER PUBLICATIONS

Bata, Advances in Liquid Crystal Research and Applications, vol. 2, pp. 997–1002, 1980.*

Thomas, et al.; Identification of an Opioid κ Receptor Subtype–Selective N–Substituent for (+)–)3R, 4R)–Dimethyl–4–(3–hydroxyphenyl)piperidine; J. Med. Chem. (1998) vol. 41, pp 5188–5197—XP–002153153.

Thomas, et al.; Investigation of the N–Substituent Conformation Governing Potency and μ Receptor Subtype–Selectivity in (+)–(3R, 4R)–Dimethyl–4–(3–hydroxyphenyl)–piperidine Opioid Antagonists; J. Med. Chem. (1998), vol. 41, pp 1980–1990.

Mitch, et al.; 3,4–Dimethyl–4–(3–hydroxyphenyl)piperidines: Opioid Antagonists with Potent Anorectant Activity; J. Med. Chem. (1993) 2842–2850.

Zimmerman; Structure–Activity Relationship of trans–3, 4–dimethyl–4–(3–hydroxypheyl)piperidine Antagonists for μ– and κ–Opioid Receptors; J. Med. Chem. (1993) 283–2850.

* cited by examiner

Primary Examiner—Zinna Northington Davis
(74) Attorney, Agent, or Firm—P. C. Richardson; P. H. Ginsburg; J. W. Appleman

(57) ABSTRACT

There is provided a compound of formula I,

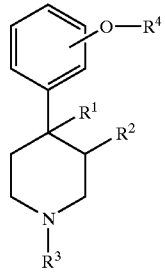

I wherein R¹, R², R³ and R⁴ have meanings given in the description, which are useful in the prophylaxis and in the treatment of pruritus.

12 Claims, No Drawings

4-ARYLPIPERIDINE DERIVATIVES FOR THE TREATMENT OF PRURITUS

This application claims priority under 35 U.S.C. 119 from application GB 9912415.8, filed May 28, 1999.

FIELD OF THE INVENTION

This invention relates to novel 4-phenylpiperidines having utility in the treatment of pruritic dermatoses including allergic dermatitis and atopy in animals and humans, and processes for the preparation of and intermediates used in the preparation of such compounds.

BACKGROUND OF THE INVENTION

Itching or pruritus is a common dermatological symptom which can give rise to considerable distress, in both humans and animals. Pruritus is often associated with inflammatory skin disease which can commonly be caused by hypersensitivity reactions, such as reaction to insect bites e.g. flea bites, or to environmental allergens such as house dust mite or pollen; or by bacterial and fungal infections of the skin or ectoparasite infections. Previous treatments for pruritus include the use of corticosteroids and antihistamines, however both have undesired side effects. Other therapies include the use of essential fatty acid dietary supplements which are slow to act and offer only limited efficacy against allergic dermatitis. A variety of emollients such as soft paraffin, glycerine and lanolin are also employed but with limited success and there is a continuing need for an effective remedy.

Certain 1,3,4-trisubstituted 4-aryl-piperidine derivatives are disclosed in GB-A-1525584 as potent narcotic antagonists which also display analgesic properties. These compounds are also claimed in EP-B-0287339 as opioid antagonists which block the effect of agonists at the mu or kappa receptors having potential utility in treating a variety of disorders associated with these receptors such as eating disorders, opiate overdose, depression, smoking, alcoholism, sexual dysfunction, shock, stroke, spinal damage and head trauma; utility as an appetite suppressant for weight loss has also been suggested. Further related 1-N-substituted-4-aryl piperidines are disclosed in EP-A-0506468 and EP-A-0506478. Potential utility is suggested in preventing peripherally mediated undesired opiate effects and in relieving the symptoms of idiopathic constipation and irritable bowel syndrome.

SUMMARY OF THE INVENTION

According to the present invention we provide novel 4-phenylpiperidines which are potent and effective antipruritic agents.

Thus, the present invention provides compounds of formula I:

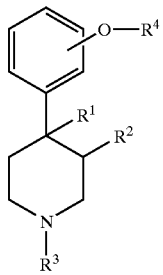

wherein
$R^1$ and $R^2$ are each independently H or $C_{1-4}$ alkyl;
$R^3$ represents aryl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and $-N(R^{5a})(R^{5b})$), $C_{1-10}$ alkyl, $C_{3-10}$ alkenyl or $C_{3-10}$ alkynyl wherein said alkyl, alkenyl or alkynyl groups are optionally substituted and/or terminated by one or more substituents selected from $OR^{5c}$, $S(O)_n R^{5d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{6a})S(O)_2R^7$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $-W-A^1-N(R^{6b})(R^{6c})$;
n is 0, 1 or 2;
W represents a single bond, C(O) or $S(O)_p$;
$A^1$ represents a single bond or $C_{1-10}$ alkylene;
provided that when both W and $A^1$ represent single bonds, then the group $-N(R^{6b})(R^{6c})$ is not directly attached to an unsaturated carbon atom;
p is 0, 1 or 2;
$R^{5a}$ to $R^{5d}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;
provided that $R^{5d}$ does not represent H when n represents 1 or 2;
$R^{6a}$ to $R^{6c}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $Het^3$, or $R^{6b}$ and $R^{6c}$ together represent unbranched $C_{2-6}$ alkylene which alkylene group is optionally interrupted by O, S and/or an $N(R^8)$ group and is optionally substituted by one or more $C_{1-4}$ alkyl groups;
$R^7$ represents $C_{1-6}$ alkyl, $C_{3-8}$ cycloalkyl, $C_{1-4}$ alkylphenyl or aryl, which four groups are optionally substituted by or one or more substituents selected from $C_{1-4}$ alkyl, $C_{1-4}$ alkoxy, OH, nitro, amino or halo;
$R^8$ represents H, $C_{1-6}$ alkyl, $C_{3-8}$ cycloalkyl, $A^2$-($C_{3-8}$ cycloalkyl) or $A^2$-aryl;

A² represents $C_{1-6}$ alkylene;

Het¹, Het² and Het³ independently represent 3- to 8-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms); and R⁴ represents H, $C_{1-5}$ alkyl, $C_{1-12}$ alkanoyl, (pyridin-3-yl)carbonyl or (pyridin-4-yl)carbonyl (which latter two groups are optionally in the pyridine N-oxide form);

or pharmaceutically, or veterinarily, acceptable derivatives thereof;

provided that, when the group OR⁴ is attached to the benzene ring at the meta-position relative to the piperidine ring and the piperidine is not in the N-oxide form, then:

(a) when R¹ and R² both represent $C_{1-4}$ alkyl, then R³ does not represent:
$C_{1-8}$ alkyl (optionally terminally substituted by $C_{4-8}$ cycloalkyl);
unsubstituted $C_{3-8}$ alkenyl;
unsubstituted $C_{3-8}$ alkynyl;
$C_{1-3}$ alkyl, terminally substituted by phenyl, phenoxy, —S-phenyl, —N(H)-phenyl or —N($C_{1-4}$ alkyl)-phenyl, furan-2-yl or thiophen-2-yl;
$C_{1-4}$ alkyl, terminally substituted by an OH group and a further group selected from phenyl, furan-2-yl and thiophen-2-yl; or
$C_{3-5}$ alkenyl, terminally substituted by phenyl, furan-2-yl or thiophen-2-yl, where the position of unsaturation is at the carbon atoms that are α,β to the phenyl, furan-2-yl or thiophen-2-yl group;

all of which phenyl, phenoxy and phenylthio groups are optionally substituted by one or two substituents selected from OH, $C_{1-3}$ alkyl, $C_{1-3}$ alkoxy, halo, nitro, amino and CF₃; and all of which furanyl and thiophenyl groups are optionally substituted by a methyl group; and (b) when R¹ represents methyl, and:
(i) R² represents $C_{1-4}$ alkyl and R⁴ represents H or $C_{1-4}$ alkanoyl, then R³ does not represent:
unsubstituted $C_{3-8}$ alkyl;
unsubstituted $C_{4-8}$ alkenyl;
$C_{3-8}$ alkyl, substituted by an unsubstituted $C_{4-8}$ cycloalkyl group;
$C_2$ alkyl, terminally substituted by an unsubstituted $C_{5-9}$ cycloalkanoyl, an unsubstituted $C_{2-6}$ alkanoyl group or an unsubstituted thiophenyl group;
$C_{4-9}$ alkyl (optionally substituted at 4- to 9-C position by $C_{4-8}$ cycloalkyl) or $C_{5-9}$ alkenyl, which alkyl or alkenyl groups are substituted at the 3-C position by OH, $C_{1-6}$ alkoxy, oxy-$C_{1-3}$-alkylphenyl or $C_{2-5}$ alkanoyloxy (which latter three groups are all unsubstituted); or
$C_3$ alkyl, terminally substituted by (1) OH, $C_{1-6}$ alkoxy, oxy-$C_{1-3}$-alkylphenyl or $C_{2-5}$ alkanoyloxy (which latter three groups are all unsubstituted) and (2) $C_{4-8}$ cycloalkyl, thiophenyl (which latter two groups are both unsubstituted); or (ii) R² represents H or $C_{1-4}$ alkyl and R⁴ represents H or $C_{1-5}$ alkyl, then (I) R³ does not represent:
methyl;
$C_{2-10}$ alkyl or $C_{4-10}$ alkenyl, both of which are substituted at the 2-, 3- or 4-C position by —W—A¹—N($R^{6b}$)($R^{6c}$) and which alkyl group only is also optionally substituted at the 3- to 10-C, 4- to 10-C or 5- to 10-C position (respectively) by unsubstituted $C_{3-8}$ cycloalkyl or unsubstituted phenyl; or
$C_{1-4}$ alkyl, which alkyl group is terminally substituted by —W—A¹—N($R^{6b}$)($R^{6c}$), and is also optionally terminally substituted by unsubstituted $C_{3-8}$ cycloalkyl or unsubstituted phenyl;
in which, in both cases, W is a single bond, A¹ is a single bond or $C_{1-3}$ alkylene, $R^{6b}$ or $R^{6c}$ is H or unsubstituted $C_{1-10}$ alkyl and $R^{6b}$ or $R^{6c}$ (as appropriate) is H, $C_{3-8}$ cycloalkyl, $C_{1-10}$ alkyl, $C_{3-10}$ alkenyl, phenyl or $C_{1-3}$ alkylphenyl (which latter five groups are all unsubstituted); or (II) R³ does not represent:
$C_{1-10}$ alkyl or $C_{3-10}$ alkenyl, both of which are substituted at the 1- to 5-C (as appropriate) by unsubstituted $C_{1-6}$ alkoxycarbonyl or W—A¹—N($R^{6b}$)($R^{6c}$) and which alkyl or alkenyl groups are also optionally substituted at the 2- to 10-C, 3- to 10-C, 4- to 10-C or 5- to 10-C position (respectively) by unsubstituted $C_{3-8}$ cycloalkyl or unsubstituted phenyl; or
$C_{1-5}$ alkyl, which alkyl group is terminally substituted by an unsubstituted $C_{1-6}$ alkoxycarbonyl group or —W—A¹—N($R^{6b}$)($R^{6b}$), and is optionally terminally substituted by unsubstituted phenyl or unsubstituted $C_{3-8}$ cycloalkyl;
in which, in both cases, W is —C(O)—, A¹ is a single bond, $R^{6b}$ or $R^{6c}$ is H or unsubstituted $C_{1-3}$ alkyl and $R^{6b}$ or $R^{6c}$ (as appropriate) is H, $C_{1-10}$ alkyl, $C_{3-10}$ alkenyl, $C_{3-8}$ cycloalkyl, phenyl, $C_{1-3}$ alkylphenyl (which latter five groups are all unsubstituted), linear $C_{1-4}$ alkyl (which latter group is terminally substituted by amino), or $R^{6b}$ and $R^{6c}$ together represent unsubstituted $C_{3-5}$ alkylene;

(c) when R¹ and R² both represent methyl and are in the mutually trans-configuration and R⁴ represents H or $C_{1-4}$ alkanoyl, then R³ does not represent:
unsubstituted $C_{1-8}$ alkyl;
unsubstituted $C_{3-8}$ alkenyl;
unsubstituted $C_{3-8}$ alkynyl;
$C_{1-6}$ alkyl, terminally substituted by an unsubstituted $C_{3-8}$ cycloalkyl group;
$C_{1-3}$ alkyl, terminally substituted by $C_{3-8}$ cycloalkanoyl, $C_{3-8}$ cycloalkoxy, $C_{3-8}$ cycloalkyl, naphthyl, thiophenyl, thiophenoxy, furanyl, furanoxy, tetrahydrofuranyl, pyridinyl or pyridinyloxy (which latter eleven groups are all unsubstituted), phenyl or phenoxy (which latter two groups are optionally substituted by one or more substituents selected from halo, $C_{1-4}$ alkyl and $C_{1-4}$ alkoxy); or
$C_{1-4}$ alkyl, terminally substituted by an OH group and by one of the following groups: phenyl (which latter group is optionally substituted by one or more substituents selected from halo, $C_{1-4}$ alkyl and $C_{1-4}$ alkoxy), $C_{1-2}$ alkylphenyl, $C_{3-8}$ cycloalkyl, thiophenyl, furanyl or pyridinyl (which latter four groups are all unsubstituted);

in all of which provisos, optionally substituted alkyl, alkenyl and alkynyl groups are not interrupted by one or more O and/or S atoms;

which compounds are referred to together hereinafter as "the compounds of the invention".

DETAILED DESCRIPTION OF THE INVENTION

In the definitions used herein, alkyl, alkylene, alkoxy, alkoxy carbonyl, alkanoyl, alkanoyloxy, alkenyl, alkynyl and the alkyl parts of alkylphenyl and aryl alkoxy groups may, when there is a sufficient number of carbon atoms, be straight or branched-chain and/or optionally interrupted by one or more oxygen and/or sulfur atom(s). The term halo includes fluoro, chloro, bromo or iodo. The term "aryl" includes optionally substituted phenyl, naphthyl and the like, and "aryloxy" includes optionally substituted phenoxy and naphthyloxy and the like. Unless otherwise specified, aryl and aryloxy groups are optionally substituted by one or more (e.g. one to three) substituents selected from OH, nitro, amino, halo, CN, $CH_2CN$, $CONH_2$, $C_{1-4}$ alkyl, $C_{1-4}$ alkoxy $C_{1-4}$ alkoxy carbonyl and $C_{1-5}$ alkanoyl (which latter four groups are optionally substituted by one or more halo atoms).

The heterocyclic rings that $Het^1$, $Het^2$ and $Het^3$ represent may be fully saturated, partially unsaturated and/or wholly or partially aromatic in character. Specific rings that may be mentioned include: for $Het^1$, dioxane, dioxolane, morpholine, piperidine, perhydroazepine, pyrazole, pyridine, triazole, tetrahydrofuran, tetrahydropyran, pyrrole, pyrrollidine or tetrazole; for $Het^2$, tetrahydropyran.

For the avoidance of doubt, when Het ($Het^1$, $Het^2$ and $Het^3$) groups are at least part-saturated, possible points of substitution include the atom (e.g. the carbon atom) at the point of attachment of the Het group to the rest of the molecule. Het groups may also be attached to the rest of the molecule via a heteroatom.

The piperidine moiety in compounds of formula I may be in N-oxidised form. Sulfur atoms that may interrupt (e.g. alkyl) substituents in compounds of formula I may be present in oxidised form (e.g. as sulfoxides or sulfones). All $Het^1$, $Het^2$ and $Het^3$ groups may also be in N- or S-oxidized forms.

The term "pharmaceutically, or veterinarily, acceptable derivatives" includes non-toxic salts. Salts which may be mentioned include: acid addition salts, for example, salts formed with sulfuric, hydrochloric, hydrobromic, phosphoric, hydroiodic, sulfamic, organo-sulfonic, citric, carboxylic (e.g. acetic, benzoic, etc.), maleic, malic, succinic, tartaric, cinnamic, ascorbic and related acids; base addition salts; salts formed with bases, for example, the sodium, potassium and $C_{1-4}$ alkyl ammonium salts.

The compounds of the invention may also be in the form of quaternary ammonium salts, e.g. at the piperdine moiety, which salts may be formed by reaction with a variety of alkylating agents, such as an alkyl halide or an ester of sulfuric, or an aromatic sulfonic acid.

The compounds of the invention may exhibit tautomerism. All tautomeric forms of the compounds of formula I are included within the scope of the invention.

The compounds of the invention contain one or more asymmetric centres and thus they can exist as enantiomers and diastereomers. Diastereoisomers may be separated using conventional techniques e.g. by fractional crystallisation or chromatography. The various stereoisomers may be isolated by separation of a racemic or other mixture of the compounds using conventional techniques e.g. fractional crystallisation or HPLC. The desired optical isomers may be prepared by reaction of the appropriate optically active starting materials under conditions which will not cause racemisation or epimerisation. Alternatively, the desired optical isomers may be prepared by resolution, either by HPLC of the racemate using a suitable chiral support or, where appropriate, by fractional crystallisation of the diastereoisomeric salts formed by reaction of the racemate with a suitable optically active acid or base. The invention includes the use of both the separated individual isomers as well as mixtures of isomers.

Also included within the scope of the invention are radiolabelled derivatives of compounds of formula I which are suitable for biological studies.

According to a further aspect of the invention, there is provided a compound of formula I, as hereinbefore defined, with the additional proviso that when $OR^4$ is OH, and is attached to the benzene ring at the meta-position relative to the piperidine ring, which piperidine ring is not in N-oxidised form, then $R^3$ represents:

optionally substituted aryl;

optionally substituted $C_{3-10}$ alkenyl or $C_{3-10}$ alkynyl (which two groups are both interrupted by at least one oxygen and/or sulfur atoms);

$C_{2-10}$ alkyl, interrupted by at least two oxygen atoms and/or at least one sulfur atom;

$C_{1-10}$ alkyl, $C_{3-10}$ alkenyl or $C_{3-10}$ alkynyl, which groups are all optionally interrupted by one or more oxygen and/or sulfur atoms, and are substituted and/or terminated by one or more of:

$S(O)_n R^{5d}$, $N(R^{6a})S(O)_2 R^7$, $Het^1$ (substituted by one or more substituents selected from nitro, amino and $C_{1-5}$ alkanoyl (which latter group is optionally substituted by one or more halo atoms)), aryl (substituted by one or more substituents selected from nitro, amino and $C_{1-5}$ haloalkanoyl) or adamantyl (which latter group is substituted by one or more of the relevant substituents identified hereinbefore);

or $OR^{5c}$, in which $R^{5c}$ represents $C_{7-10}$ alkyl, $C_{3-10}$ alkenyl, $C_{3-10}$ alkynyl or $Het^2$ (which latter four groups are all optionally substituted by one or more of the relevant substituents identified hereinbefore), or $R^{5c}$ represents $C_{1-10}$ alkyl, $C_{1-4}$ alkylphenyl, $C_{3-8}$ cycloalkyl or aryl (which latter four groups are all substituted by one or more of the relevant substituents identified hereinbefore);

—W—$A^1$—$N(R^{6b})(R^{6c})$, in which $R^{6b}$ and/or $R^{6c}$ independently represent $C_{1-4}$ alkylphenyl (which latter group is optionally substituted by one or more of the relevant substituents identified hereinbefore), $C_{1-10}$ alkyl, $C_{3-10}$ alkenyl, $C_{3-10}$ alkynyl, $C_{3-8}$ cycloalkyl (which latter four groups are all substituted by one or more of the relevant substituents identified hereinbefore), or aryl (substituted by one or more substituents selected from nitro, amino and $C_{1-5}$ haloalkanoyl);

which compounds may also be termed "compounds of the invention".

According to a further aspect of the invention, there is provided a compound of formula I, as hereinbefore defined, with the additional proviso that when $OR^4$ is $O-C_{1-4}$ alkyl, and is attached to the benzene ring at the meta-position relative to the piperidine ring, which piperidine ring is not in N-oxidised form, then $R^3$ does not represent:

straight or branched-chain $C_{1-10}$ alkyl (optionally substituted by one or more substituents selected from unsubstituted aryl or unsubstituted $C_{3-8}$ cycloalkyl);

which compounds may also be termed "compounds of the invention".

Preferred compounds of the invention include those wherein:

The group $OR^4$ is attached to the benzene ring in the position meta-relative to the piperidine group;

$R^1$ represents $C_{1-2}$ alkyl;

$R^2$ represents H or $C_{1-2}$ alkyl;

$R^3$ represents aryl (optionally substituted by one or more substituents selected from $C_{1-2}$ alkyl, $C_{1-2}$ alkoxy, halo, nitro and —$N(R^{5a})(R^{5b})$), $C_{1-8}$ alkyl, $C_{3-8}$ alkenyl or $C_{3-8}$ alkynyl wherein said alkyl, alkenyl or alkynyl groups are optionally interrupted by one or more oxygen atoms and/or are substituted and/or terminated by one or more substituents selected from $OR^{5c}$, $S(O)_nR^{5d}$, CN, halo, $C_{1-4}$ alkoxy carbonyl, $C_{4-6}$ cycloalkyl, $C_{5-7}$ cycloalkanoyl, $Het^1$, aryl (which latter group is optionally substituted by one or more substituents selected from OH, $C_{1-2}$ alkyl, $C_{1-2}$ alkoxy or halo), or —$W$—$A^1$—$N(R^{6b})(R^{6c})$;

W represents a single bond or C(O);

$A^1$ represents a single bond or $C_{1-3}$ alkylene;

$R^{5a}$ to $R^{5d}$ each independently represent H, $C_{1-6}$ alkyl, $C_{3-6}$ alkenyl, $C_{3-6}$ alkynyl, $C_{4-8}$ cycloalkyl, $C_{1-2}$ alkylphenyl, aryl or $Het^2$;

$R^{6b}$ and $R^{6c}$ independently represent H, $C_{1-2}$ alkyl, $Het^3$, or $R^{6b}$ and $R^{6c}$ together represent unbranched $C_{2-6}$ alkylene which alkylene group is optionally interrupted by O or S and is optionally substituted by one or more $C_{1-2}$ alkyl groups;

$Het^1$, $Het^2$ and $Het^3$ independently represent 5- to 7-membered heterocyclic groups, which groups contain at least one heteroatom selected from oxygen, sulfur and/or nitrogen, which groups are optionally fused to a benzene ring, and which groups are optionally substituted in the heterocyclic and/or fused benzene ring part by one or more substituents selected from OH, =O and $C_{1-2}$ alkyl (which latter group is optionally substituted by one or more halo atoms);

$R^4$ represents H or $C_{1-5}$ alkanoyl.

More preferred compounds of the invention include those wherein:

$R^1$ represents methyl;

$R^2$ represents H or methyl;

$R^3$ represents phenyl (optionally substituted by one or more substituents selected from methyl, methoxy and —$N(CH_3)_2$), linear $C_{1-7}$ alkyl or linear $C_{1-7}$ alkenyl, which alkyl or alkenyl groups are optionally interrupted by one or more oxygen atoms and/or are optionally substituted and/or terminated by one or more substituents selected from $OR^{5c}$, $S(O)_nR^{5d}$, $C_{1-2}$ alkoxy carbonyl, $C_{4-6}$ cycloalkyl, $Het^1$ or —$C(O)N(R^{6b})(R^{6c})$;

$R^{5c}$ and $R^{5d}$ each independently represent H, $C_{1-3}$ alkyl, $C_{3-4}$ alkenyl, $C_{5-7}$ cycloalkyl, phenyl, naphthyl or $Het^2$;

$R^{6b}$ and $R^{6c}$ together represent unbranched $C_{4-6}$ alkylene which alkylene group is optionally interrupted by O and is optionally substituted by one or more $C_{1-2}$ alkyl groups;

$Het^1$ and $Het^2$ independently represent 5- to 7-membered heterocyclic groups, which groups contain at least one heteroatom selected from oxygen, sulfur and/or nitrogen, and which groups are optionally substituted by one or more $C_{1-2}$ alkyl groups.

Particularly preferred compounds of the invention include those wherein:

$R^1$ and $R^2$ represent methyl groups in the mutually trans configuration;

$R^4$ represents H.

Preferred compounds of the invention include the compounds of the Examples described hereinafter.

Thus, according to a further aspect of the invention, there is provided a compound of formula I which, irrespective of any of the foregoing definitions and/or provisos, is:

(±)-3-{1-[2-(cyclohexyloxy)ethyl]-trans-3,4-dimethylpiperidinyl}phenol;

(±)-3-{1-[2-(1,3-dioxan-2-yl)ethyl]-trans-3,4-dimethylpiperidinyl}phenol;

(±)-3-[1-(3-hydroxypropyl)-trans-3,4-dimethylpiperidinyl]phenol;

(±)-3-{1-[3-(allyloxy)propyl]-trans-3,4-dimethylpiperidinyl}phenol;

(±)-3-[1-(2-ethoxyethyl)-trans-3,4-dimethylpiperidinyl]phenol;

(±)-3-[1-(3-tetrahydro-3-furanylpropyl)-trans-3,4-dimethylpiperidinyl]phenol;

(±)-3-{1-[2-(2-methoxyethoxy)ethyl]-trans-3,4-dimethylpiperidinyl}phenol;

(±)-3-[1-(2-methoxyethyl)-trans-3,4-dimethylpiperidinyl]phenol;

(±)-3-{1-[2-(vinyloxy)ethyl]-trans-3,4-dimethylpiperidinyl}phenol;

(±)-3-(1-{2-[2-(2-hydroxyethoxy)ethoxy]ethyl}-trans-3,4-dimethylpiperidinyl)phenol;

(±)-3-{1-[3-(tetrahydro-2H-pyran-2-yloxy)propyl]-trans-3,4-dimethylpiperidinyl}phenol;

(±)-3-[1-(3-tetrahydro-2H-pyran-2-ylpropyl)-trans-3,4-dimethylpiperidinyl]phenol;

(±)-3-{1-[3-(1,3-dioxan-2-yl)propyl]-trans-3,4-dimethylpiperidinyl}phenol;

(±)-3-[1-(3,3-dimethoxypropyl)-trans-3,4-dimethylpiperidinyl]phenol;

(±)-3-{1-[2-(2-hydroxyethoxy)ethyl]-trans-3,4-dimethylpiperidinyl}phenol;

(±)-3-{1-[2-(1,3-dioxolan-2-yl)ethyl]-trans-3,4-dimethylpiperidinyl}phenol;

(±)-3-{1-[4-(1,3-dioxolan-2-yl)butyl]-trans-3,4-dimethylpiperidinyl}phenol;

(±)-3-{1-[2-(2,5,5-trimethyl-1,3-dioxan-2-yl)ethyl]-trans-3,4-dimethylpiperidinyl}phenol;

(±)-3-{1-[2-(tetrahydro-2H-pyran-2-yloxy)ethyl]-trans-3,4-dimethylpiperidinyl}phenol;

(±)-3-[1-(5-hydroxypentyl)-trans-3,4-dimethylpiperidinyl]phenol;

(±)-3-[1-(3-tetrahydro-2H-pyran-4-ylpropyl)-trans-3,4-dimethylpiperidinyl]phenol;

(±)-3-{1-[2-(2-naphthyloxy)ethyl]-trans-3,4-dimethylpiperidinyl}phenol;

(±)-3-[1-(2-isopropoxyethyl)-trans-3,4-dimethylpiperidinyl]phenol; 3-[1-(2-propoxyethyl)-trans-3,4-dimethylpiperidinyl]phenol;

(±)-3-{1-[2-(cyclopentyloxy)ethyl]-trans-3,4-dimethylpiperidinyl}phenol;

(±)-3-[1-(3-tetrahydro-2-furanylpropyl)-trans-3,4-dimethylpiperidinyl]phenol;

(±)-3-{1-[2-(cyclohexylsulfanyl)ethyl]-trans-3,4-dimethylpiperidinyl}phenol;

(±)-3-{1-[2-(ethylsulfanyl)ethyl]-trans-3,4-dimethylpiperidinyl}phenol;

(±)-3-{1-[2-(ethylsulfinyl)ethyl]-trans-3,4-dimethylpiperidinyl}phenol;

(±)-3-{1-[2-(ethylsulfonyl)ethyl]-trans-3,4-dimethylpiperidinyl}phenol;

(±)-3-{1-[3-(1H-1,2,3,4-tetrazol-1-yl)propyl]-trans-3,4-dimethylpiperidinyl}phenol;

(±)-3-{1-[3-(1H-pyrazol-1-yl)propyl]-trans-3,4-dimethylpiperidinyl}phenol;

(±)-3-{1-[3-(4-pyridinyl)propyl]-trans-3,4-dimethylpiperidinyl}phenol;

(±)-3-{1-[3-(1H-1,2,4-triazol-1-yl)propyl]-trans-3,4-dimethylpiperidinyl}phenol;

(±)-3-{1-[3-(1H-pyrrol-1-yl)propyl]-trans-3,4-dimethylpiperidinyl}phenol;

(±)-3-[trans-3,4-dimethyl-4-(3-hydroxyphenyl)piperidinyl]-1-(4-morpholinyl)-1-propanone;

3-{1-[3-(4-morpholinyl)propyl]-trans-3,4-dimethylpiperidinyl}phenol;

3-{1-[2-(1-azepanyl)ethyl]-trans-3,4-dimethylpiperidinyl}phenol;

3-{1-[2-(4-morpholinyl)ethyl]-trans-3,4-dimethylpiperidinyl}phenol;

3-{1-[2-(1-piperidinyl)ethyl]-trans-3,4-dimethylpiperidinyl}phenol;

3-{1-[2-(1-pyrrolidinyl)ethyl]-trans-3,4-dimethylpiperidinyl}phenol;

3-{1-[3-(1-piperidinyl)propyl]-trans-3,4-dimethylpiperidinyl}phenol;

(±)-3-[1-(3-methoxyphenyl)-trans-3,4-dimethylpiperidinyl]phenol; or (±)-3-{1-[4-(dimethylamino)phenyl]-trans-3,4-dimethylpiperidinyl}phenol; or (±)-methyl 3-[trans-3,4-dimethyl-4-(3-hydroxyphenyl)piperidinyl]propionate, which compounds may also be termed "compounds of the invention".

According to a further aspect of the invention there is provided processes for the preparation of compounds of the invention, as illustrated below.

The following processes are illustrative of the general synthetic procedures which may be adopted in order to obtain the compounds of the invention.

1. Compounds of formula I wherein $R^3$ represents $C_1$ alkyl optionally substituted by $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or $R^3$ represents $C_{2-10}$ alkyl, $C_{3-10}$ alkenyl or $C_{3-10}$ alkynyl (which three groups are all optionally substituted by one or more of the relevant substituents identified hereinbefore in respect of $R^3$), which alkyl, alkenyl or alkynyl groups are attached to the piperidine nitrogen atom via a $CH_2$ group, wherein $Het^1$ is as hereinbefore defined, may be prepared by reduction of a corresponding compound of formula II,

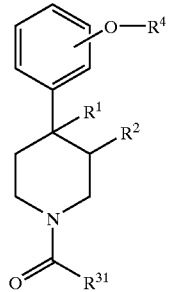

wherein $R^{31}$ represents H, $C_{3-8}$ cycloalkyl, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), $C_{1-9}$ alkyl, $C_{2-9}$ alkenyl or $C_{2-9}$ alkynyl, which alkyl, alkenyl or alkynyl groups are optionally substituted and/or terminated by one or more substituents selected from $OR^{5c}$, $S(O)_n^{5d}$, CN, halo, $C_{1-6}$ alkoxy carbonyl, $C_{2-6}$ alkanoyl, $C_{2-6}$ alkanoyloxy, $C_{3-8}$ cycloalkyl, $C_{4-9}$ cycloalkanoyl, $N(R^{6a})S(O)_2R^7$, $Het^1$, aryl, adamantyl (which latter two groups are optionally substituted by one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)), or —W—$A^1$—$N(R^{6b})(R^{6c})$, and $R^1$, $R^2$, $R^4$, $R^{5c}$, $R^{5d}$, $R^{6a}$ to $R^{6c}$, $R^7$, $Het^1$, n, W and $A^1$ are as hereinbefore defined, using a suitable reducing agent (e.g. lithium aluminium hydride or a borane derivative), for example as described hereinbefore.

Compounds of formula II may be prepared by reaction of a corresponding compound of formula III,

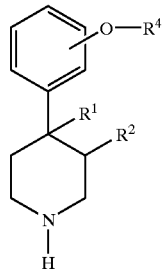

wherein $R^1$, $R^2$ and $R^4$ are as hereinbefore defined with a compound of formula IV, $R^{31}CO_2H$      IV or a suitable (e.g. carboxylic acid) derivative thereof (e.g. an acid halide or anhydride), wherein $R^{31}$ is as hereinbefore defined, using coupling conditions known to those skilled in the art.

Compounds of formula III may be prepared from appropriate precursors by analogy with other methods disclosed herein that describe the production of compounds of formula I.

2. Compounds of formula I in which $R^4$ represents $C_{1-12}$ alkanoyl, (pyridin-3-yl)carbonyl or (pyridin-4-yl)carbonyl (which latter two groups are optionally in the pyridine N-oxide form) may be prepared by reaction of a corresponding compound of formula I in which $R^4$ represents H with a compound of formula V, $$R^{41}\text{—}CO_2H \qquad \qquad V$$

or a suitable (e.g. carboxylic acid) derivative thereof (e.g. an acid halide or anhydride), wherein $R^{41}$ represents $C_{1-11}$ alkyl, pyridin-3-yl or pyridin-4-yl (which latter two groups are optionally in the pyridine N-oxide form), using coupling conditions known to those skilled in the art.

3. Compounds of formula I may also be prepared by reaction of a corresponding compound of formula III, as hereinbefore defined, with a compound of formula VI, $$R^3\text{—}L^1 \qquad \qquad VI$$

wherein $L^1$ represents a leaving group such as halo, alkanesulfonate, perfluoroalkanesulfonate or arenesulfonate) and $R^3$ is as hereinbefore defined, under conditions that are well known to those skilled in the art, which include, for example, alkylation at between room temperature and reflux temperature in the presence of a reaction-inert organic solvent (e.g. N,N-dimethylformamide) and a suitable base (e.g. $NaHCO_3$), and arylation at between room temperature and reflux temperature in the presence of a suitable catalyst system (e.g. tris(dibenzylideneacetone)palladium(0) combined with tri-o-tolylphosphine), an appropriate strong base (e.g. sodium tert-butoxide) and a reaction-inert solvent (e.g. toluene).

4. Compounds of formula I wherein $R^3$ represents $C_1$ alkyl, which, in place of being optionally substituted by the substituents as defined hereinbefore, is instead optionally substituted by $R^{31}$, wherein $R^{31}$ is as hereinbefore defined, may be prepared by reaction of a corresponding compound of formula III, as hereinbefore defined, with a compound of formula VII, $$R^{31}CHO \qquad \qquad VII$$

wherein $R^{31}$ is as hereinbefore defined, for example in the presence of a suitable reducing agent (e.g. sodium borohydride, sodium cyanoborohydride or sodium triacetoxyborohydride) and an appropriate solvent (e.g. methanol).

5. Compounds of formula I wherein $R^3$ is a $C_{1-10}$ alkyl, $C_{4-10}$ alkenyl or $C_{4-10}$ alkynyl group that is fully saturated from 1- to 3-C (relative to the piperidine N-atom), and which $R^3$ group is substituted at 2-C (relative to the piperidine N-atom) by $S(O)R^{5d}$, $S(O)_2R^{5d}$, alkanoyl, cycloalkanoyl, alkoxy carbonyl, CN, —C(O)—$A^1$—N($R^{6b}$)($R^{6c}$), —S(O)—$A^1$—N($R^{6b}$)($R^{6c}$), or —S(O)$_2$—$A^1$—N($R^{6b}$)($R^{6c}$), wherein $R^{5d}$, $R^{6b}$, $R^{6c}$ and $A^1$ are as hereinbefore defined, may be prepared by reaction of a corresponding compound of formula III, as hereinbefore defined, with a compound of formula VIII, $$R^{3a}\text{—}Z \qquad \qquad VIII$$

wherein $R^{3a}$ represents $R^3$ as hereinbefore defined except that it does not represent aryl, and that the $R^{3a}$ chain contains an additional carbon-carbon double bond $\alpha,\beta$ to the Z-substituent, and Z represents $S(O)R^{5d}$, $S(O)_2R^{5d}$, alkanoyl, cycloalkanoyl, alkoxy carbonyl, CN, —C(O)—$A^1$—N($R^{6b}$)($R^{6c}$), —S(O)—$A^1$—N($R^{6b}$)($R^{6c}$) or —S(O)$_2$—$A^1$—N($R^{6b}$)($R^{6c}$), wherein $R^{5d}$, $R^{6b}$, $R^{6c}$ and $A^1$ are as hereinbefore defined, for example at between room and reflux temperature in the presence of a reaction-inert solvent (e.g. THF).

Compounds of formulae IV to IX, and derivatives thereof, when not commercially available or not subsequently described, may be obtained either by analogy with the processes described herein, or by conventional synthetic procedures, in accordance with standard techniques, from readily available starting materials using appropriate reagents and reaction conditions (see, for example, "Comprehensive Organic Transformations—A Guide to Functional Group Preparations", R. C. Larrock, VCH (1989), or "Advanced Organic Chemistry—Reactions, Mechanism and Structure", 4$^{th}$ edition, J. March, Wiley-Interscience (1992)). For example, compounds of formula I in which $R^4$ represents H may be made according to or by analogy with the procedures disclosed in the publications mentioned above relating to 4-arylpiperidine-based compounds.

Substituents on alkyl, heterocyclic and aryl groups in the above-mentioned compounds may also be introduced, removed and interconverted, using techniques which are well known to those skilled in the art. For example, nitro may be reduced to amino, OH may be alkylated to give alkoxy, alkoxy may be hydrolysed to OH, alkenes may be hydrogenated to alkanes, halo may be hydrogenated to H, etc.

The skilled person will also appreciate that other various standard substituent or functional group interconversions and transformations within certain compounds of formula I will provide other compounds of formula I.

The compounds of the invention may be isolated from their reaction mixtures using conventional techniques.

It will be appreciated by those skilled in the art that, in the course of carrying out the processes described above, the functional groups of intermediate compounds may need to be protected by protecting groups.

Functional groups which it is desirable to protect include oxo, OH, amino and carboxylic acid. Suitable protective groups for oxo include acetals, ketals (e.g. ethylene ketals) and dithianes. Suitable protective groups for OH include trialkylsilyl and diarylalkylsilyl groups (e.g. tert-butyldimethylsilyl, tert-butyldiphenylsilyl or trimethylsilyl) and tetrahydropyranyl. Suitable protective groups for amino include tert-butyloxycarbonyl, 9-fluorenylmethoxycarbonyl or benzyloxycarbonyl. Suitable protective groups for carboxylic acid include $C_{1-6}$ alkyl or benzyl esters. Suitable protective groups for terminal alkynes include trialkylsilyl and diarylalkylsilyl groups (e.g. tert-butyldimethylsilyl, tert-butyldiphenylsilyl or trimethylsilyl).

The protection and deprotection of functional groups may take place before or after any of the reaction steps described hereinbefore.

Protective groups may be removed in accordance with techniques which are well known to those skilled in the art.

The use of protecting groups is fully described in "Protective Groups in Organic Chemistry", edited by J W F McOmie, Plenum Press (1973), and "Protective Groups in Organic Synthesis", 2$^{nd}$ edition, T W Greene & P G M Wutz, Wiley-Interscience (1991).

Persons skilled in the art will also appreciate that, in order to obtain compounds of formula I in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis. The procedures may be adapted as appropriate to the reactants, reagents and other reaction parameters in a manner that will be evident to the skilled person by reference to standard textbooks and to the examples provided hereinafter.

It will be appreciated by those skilled in the art that certain protected derivatives of compounds of formula I, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formula I may act as prodrugs of other compounds of formula I.

It will be further appreciated by those skilled in the art, that certain moieties, known to those skilled in the art as "pro-moieties", for example as described in 'Design of Prodrugs' by H. Bundgaard, Elsevier, 1985 (the disclosure in which document is hereby incorporated by reference), may be placed on appropriate functionalities, when such functionalities are present within compounds of formula I.

All protected derivatives, and prodrugs, of compounds of formula I are included within the scope of the invention.

Pharmaceutically acceptable acid addition salts of the compounds of formula I which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formula I with the appropriate base. Both types of salt may be formed or interconverted using ion-exchange resin techniques.

The above procedures may be adapted as appropriate to the particular reactants and groups involved and other variants will be evident to the skilled chemist by reference to standard textbooks and to the examples provided hereafter to enable all of the compounds of formula I to be prepared.

The compounds of the invention are useful because they possess pharmacological activity in animals, especially mammals including humans. They are therefore indicated as pharmaceuticals and, in particular, for use as animal medicaments.

According to a further aspect of the invention there is provided the compounds of the invention (optionally a compound of formula I as defined herein but without the provisos) for use as medicaments, such as pharmaceuticals and animal medicaments.

By the term "treatment", we include both therapeutic (curative) or prophylactic treatment.

In particular, the compounds of the invention have been found to be useful in the treatment of pruritus, and conditions characterised by pruritus as a symptom.

Thus, according to a further aspect of the invention there is provided the use of the compounds of the invention (optionally a compound of formula I as defined herein but without the provisos) in the manufacture of a medicament for the treatment of pruritus or a medical condition characterised by pruritus as a symptom.

The compounds of the invention are thus expected to be useful for the curative or prophylactic treatment of pruritic dermatoses including allergic dermatitis and atopy in animals and humans. Other diseases and conditions which may be mentioned include contact dermatitis, psoriasis, eczema and insect bites.

Thus, the invention provides a method of treating or preventing pruritus or a medical condition characterised by pruritus as a symptom in an animal (e.g. a mammal), which comprises administering a therapeutically effective amount of a compound of the invention (optionally a compound of formula I as defined herein but without the provisos) to an animal in need of such treatment.

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses (see below).

While it is possible to administer a compound of the invention directly without any formulation, the compounds are preferably employed in the form of a pharmaceutical, or veterinary, formulation comprising a pharmaceutically, or veterinarily, acceptable carrier, diluent or excipient and a compound of the invention. The carrier, diluent or excipient may be selected with due regard to the intended route of administration and standard pharmaceutical, and/or veterinary, practice. Pharmaceutical compositions comprising the compounds of the invention may contain from 0.1 percent by weight to 90.0 percent by weight of the active ingredient.

The methods by which the compounds may be administered for veterinary use include oral administration by capsule, bolus, tablet or drench, topical administration as an ointment, a pour-on, spot-on, dip, spray, mousse, shampoo, collar or powder formulation or, alternatively, they can be administered by injection (e.g. subcutaneously, intramuscularly or intravenously), or as an implant. Such formulations may be prepared in a conventional manner in accordance with standard veterinary practice.

The formulations will vary with regard to the weight of active compound contained therein, depending on the species of animal to be treated, the severity and type of infection and the body weight of the animal. For parenteral, topical and oral administration, typical dose ranges of the active ingredient are 0.01 to 100 mg per kg of body weight of the animal. Preferably the range is 0.1 to 10 mg per kg.

The compositions are preferably formulated in a unit dosage form, each dosage containing from about 1 to about 500 mg, more usually about 5 to about 300 mg, of the active ingredient. The term "unit dosage form" refers to physically discreet units suitable as unitary dosages for human subjects and other mammals, each unit containing a predetermined quantity of active material calculated to produce the desired therapeutic effect, in association with a suitable pharmaceutical carrier.

In any event, the veterinary practitioner, or the skilled person, will be able to determine the actual dosage which will be most suitable for an individual patient, which may vary with the species, age, weight and response of the particular patient. The above dosages are exemplary of the average case; there can, of course, be individual instances where higher or lower dosage ranges are merited, and such are within the scope of this invention.

For veterinary use, the compounds of the invention are of particular value for treating pruritus in domestic animals such as cats and dogs and in horses.

As an alternative for treating animals, the compounds may be administered with the animal feedstuff and for this purpose a concentrated feed additive or premix may be prepared for mixing with the normal animal feed.

For human use, the compounds are administered as a pharmaceutical formulation containing the active ingredient together with a pharmaceutically acceptable diluent or carrier. Such compositions include conventional tablet, capsule and ointment preparations which are formulated in accordance with standard pharmaceutical practice.

Compounds of the invention may be administered either alone or in combination with one or more agents used in the treatment or prophylaxis of disease or in the reduction or suppression of symptoms. Examples of such agents (which are provided by way of illustration and should not be construed as limiting) include antiparasitics, e.g. fipronil, lufenuron, imidacloprid, avermectins (e.g. abamectin, ivermectin, doramectin), milbemycins, organophosphates, pyrethroids; antihistamines, e.g. chlorpheniramine, trimeprazine, diphenhydramine, doxylamine; antifungals, e.g. fluconazole, ketoconazole, itraconazole, griseofulvin, amphotericin B; antibacterials, e.g. enroflaxacin, marbofloxacin, ampicillin, amoxycillin; anti-inflammatories e.g. prednisolone, betamethasone, dexamethasone, carprofen, ketoprofen; dietary supplements, e.g. gamma-linoleic acid; and emollients. Therefore, the invention further provides a product containing a compound of the invention and a compound from the above list as a combined preparation for simultaneous, separate or sequential use in the treatment of pruritus.

The skilled person will also appreciate that compounds of the invention may be taken as a single dose on an "as required" basis (i.e. as needed or desired).

Thus, according to a further aspect of the invention there is provided a pharmaceutical, or veterinary, formulation including a compound of the invention (optionally a compound of formula I as defined herein but without the provisos) in admixture with a pharmaceutically, or veterinarily, acceptable adjuvant, diluent or carrier.

Compounds of the invention may also have the advantage that, in the treatment of human and/or animal patients, they may be more efficacious than, be less toxic than, have a broader range of activity than, be more potent than, produce fewer side effects than, be more easily absorbed than, or they may have other useful pharmacological properties over, compounds known in the prior art.

The biological activity of the compounds of the present invention was determined by the following test method.

Biological Test

The compounds of the invention are evaluated for their activity as antipruritic agents by measuring their ability to inhibit the hind leg scratching behaviour induced in rats by the administration of a known pruritogenic agent. These studies are based on the procedure described by Berendsen and Broekkamp in the European Journal of Pharmacology, 1991, 194, 201. The test is performed as follows:

Male Wistar rats (approximately 150 g body weight) are challenged with a pruritogen by subcutaneous injection of 5-methoxytryptamine hydrochloride (4 mg/3 mL/kg) dissolved in physiological saline into the scruff of the neck. At this dose a constant and quantifiable hindleg scratching response lasting up to 90 minutes is obtained.

The test compound is administered to the test animals by subcutaneous injection in an aqueous micelle formulation. The test compound is prepared in the following manner. The compound is dissolved in a vehicle (composition v/v%: glycerol formal, 24; tween 80, 17; benzyl alcohol, 1.5 and purified water to 100) then seven parts purified water is added to three parts of the above vehicle to give the aqueous micelle formulation. The compounds can be administered pre- or post-challenge or may be administered at the same time as the pruritogenic challenge.

After the pruritogen challenge has been administered, hindleg scratching is scored for each animal by recording the presence or absence of scratching during each 30 second interval as 1 or 0 scored respectively. The score for each animal is totalled after 25 minutes (maximum score 50). The efficacy of compounds is assessed by their ability to significantly reduce the score in treated groups compared to the control group.

The invention is illustrated by the following Preparations and Examples in which the following abbreviations may be used:

APCI =atmospheric pressure chemical ionisation br (in relation to NMR)=broad

DCM=dichloromethane

DMF=N,N-dimethylformamide

DMSO=dimethylsulfoxide d (in relation to time)=day d (in relation to NMR)=doublet dd (in relation to NMR)=doublet of doublets EtOAc=ethyl acetate EtOH=ethanol h=hour(s)

m (in relation to NMR)=multiplet

MeOH=methanol min=minute q (in relation to NMR)=quartet rt=room temperature s (in relation to NMR)=singlet t (in relation to NMR)=triplet THF=tetrahydrofuran TSI=thermospray ionisation When column chromatography is referred to this usually refers to a glass column packed with silica gel (40–63 µm). Pressure of about 165 kPa is generally applied and the ratio of crude product : silica gel required for purification is typically 50:1. Alternatively, an Isolute™ SPE (solid phase extraction) column or Waters Sep-Pak™ cartridge packed with silica gel may be used under atmospheric pressure. The ratio of crude product to silica gel required for purification is typically 100:1.

Hydrochloride salts of the compounds of the examples may be made by methods known to those skilled in the art of synthetic chemistry. For example, ethereal hydrochloric acid (1.0 M, 1.2 equivalent) may be added to a solution of free base in dichloromethane (1 g:100 mL), the excess solvent decanted off and the remaining precipitate washed three times with ether and dried in vacuo.

A common starting material, (±)-3-(trans-3,4-dimethylpiperidinyl)phenol, can be prepared using the procedures described in: a) Zimmerman et al, *J. Org. Chem.*, 1991, 56, 1660; b) Werner et al, *J. Org. Chem.*, 1996, 61, 587–597. All starting materials were obtained from commercial sources unless stated otherwise.

Nuclear magnetic resonance (NMR) spectral data were obtained using a Brucker AC3000, AM300 or AM400 spectrometer, the observed chemical shifts (δ) being consistent with the proposed structures. ¹H-NMR data are measured in solution in CDCl₃ unless otherwise specified. Mass spectral (MS) data were obtained on a Finnigan Mat. TSQ 7000 or a Fisons Instruments Trio 1000 spectrometer. The calculated and observed ions quoted refer to the isotopic composition of lowest mass. HPLC means high performance liquid chromatography. Room temperature means 20 to 25° C.

EXAMPLE

Example 1

(±)-3-{1-[2-(Cyclohexyloxy)ethyl]-trans-3,4-dimethylpiperidinyl}phenol

To a solution of 2-(cyclohexyloxy)ethyl-4-methylbenzenesulfonate (Preparation 18, 226 mg, 0.76 mmol) in toluene (2.0 mL) at 0° C. under a nitrogen atmosphere was added pyridine (101 mg, 1.28 mmol) and (±)-3-(trans-3,4-dimethylpiperidinyl)phenol (155 mg, 0.76 mmol). The reaction was heated at reflux for 3 hours and then at room temperature for 48 hours. The mixture was concentrated in vacuo and the crude residue was partitioned between a saturated aqueous sodium hydrogencarbonate solution (10 mL) and ethyl acetate (10 mL). The two layers were separated and the aqueous layer was extracted with dichloromethane (3×10 mL). The combined organic layers were dried over magnesium sulfate, filtered, and concentrated in vacuo to give a crude yellow oil. This was purified using a preparative silica plate, eluting with dichloromethane:methanol (95:5), to give the title compound (79 mg, 31%) as a colourless oil.

¹H-NMR: 0.85 (d, 3H), 1.10–1.24 (m, 6H), 1.25 (s, 3H), 1.55 (m, 1H), 1.60–1.68 (m, 2H), 1.71–1.95 (m, 2H), 2.05 (m, 1H), 2.35 (m, 1H), 2.60–2.92 (m, 5H), 3.05 (m, 1H), 3.25 (m, 1H), 3.68 (t, 2H), 6.68 (d, 1H), 6.78–6.83 (m, 2H), 7.11 (t, 1H). MS (TSI⁺): m/z [MH⁺] 332.5; $C_{21}H_{33}NO_2$+H requires 332.3.

Example 2

(±)-3-{1-[2-(1,3-Dioxan-2-yl)ethyl]-trans-3,4-dimethylpiperidinyl}phenol

To a solution of (±)-3-(trans-3,4-dimethylpiperidinyl)phenol (100 mg, 0.49 mmol) in N,N-dimethylformamide (2.0 mL) at room temperature under a nitrogen atmosphere was added sodium hydrogencarbonate (54 mg, 0.54 mmol) and 2-(2-bromoethyl)-1,3-dioxane (107 mg, 0.55 mmol). The solution was heated at reflux for 1 hour, cooled and then poured into a saturated sodium hydrogencarbonate solution (10 mL) and extracted with diethyl ether (4×10 mL). The combined organic layers were dried over sodium sulfate, filtered, and concentrated in vacuo to give a brown oil. This was purified by column chromatography on silica gel (10 g), eluting with a gradient of dichloromethane:ethanol:0.88 ammonia (200:8:1 to 100:8:1), to give the title compound (110 mg, 64%) as a colourless oil.

¹H-NMR: 0.78 (d, 3H), 1.28 (s, 3H), 1.35 (m, 1H), 1.60 (m, 1H), 1.72–2.20 (m, 4H), 2.25–2.60 (m, 6H), 2.85 (m, 1H), 3.68–3.78 (m, 2H), 4.02–4.12 (m, 2H), 4.60 (t, 1H), 6.65 (m, 1H), 6.75 (m, 1H), 6.81 (d, 1H), 7.15 (t, 1H). MS (TSI⁺): m/z [MH⁺] 320.0; $C_{19}H_{29}NO_3$+H requires 320.2.

Example 3

(±)-3-[1-(3-Hydroxypropyl)-trans-3,4-dimethylpiperidinyl]phenol

To a stirred solution (±)-methyl 3-[trans-3,4-dimethyl-4-(3-hydroxyphenyl)piperidinyl]propionate (Example 45, 117 mg, 0.40 mmol) in tetrahydrofuran (1 mL) at 0° C. was added lithium aluminium hydride (1.0 M solution in THF, 1.2 mL, 1.2 mmol). After 1 hour the reaction mixture was diluted with water (10 mL) and extracted with ethyl acetate (3×20 mL). The combined extracts were washed with brine (20 mL), dried over sodium sulfate, filtered and concentrated in vacuo to give the crude product. This was purified by column chromatography on silica gel, eluting with a gradient of methanol:dichloromethane:0.880 ammonia (10:990:1 to 30:970:3), to give the title compound (32 mg, 12%) as a pale yellow oil.

¹H-NMR ($C_6D_6$): 0.69 (d, 3H), 1.06 (s, 3H), 1.21–1.36 (m, 3H), 1.63 (m, 1H), 1.82 (m, 1H), 2.05–2.20 (m, 4H), 2.36 (m, 1H), 2.56 (m, 1H), 3.71 (t, 2H), 6.59 (m, 1H), 6.82 (m, 1H), 6.86 (m, 1H), 7.05–7.10 (m, 1H). MS (APCI⁺): m/z [MH⁺] 264.2; $C_{16}H_{25}NO_2$+H requires 264.2.

Example 4

(±)-3-{1-[3-(Allyloxy)propyl]-trans-3,4-dimethylpiperidinyl}phenol

To a solution of (±)-3-(trans-3,4-dimethylpiperidinyl)phenol (60 mg, 0.29 mmol) in N,N-dimethylformamide (5.0 mL) at room temperature was added sodium hydrogencarbonate (27 mg, 0.32 mmol), sodium iodide (48 mg, 0.32 mmol) and 3-allyloxypropyl chloride (43 mg, 0.32 mmol). The solution was heated at 120° C. for 1 hour, cooled and then water (10 mL) was added. The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min⁻¹; employing U.V. detection at 275 nm; eluant gradient of acetonitrile:0.05 M aqueous ammonium acetate solution (90:10 to 10:90) to afford the title compound (58 mg, 66%) as its acetate salt.

¹H-NMR (selected data from the acetate salt): 0.78 (d, 3H), 1.28 (s, 3H), 1.60 (m, 1H), 1.78–1.90 (m, 2H), 3.45 (t, 2H), 3.91 (m, 2H), 5.14 (t, 1H), 5.23 (d, 1H), 5.85 (m, 1H), 6.61 (d, 1H), 6.70–6.81 (m, 2H), 7.10 (t, 1H). MS (TSI⁺): m/z [MH⁺] 304.5; $C_{19}H_{29}NO_2$+H requires 304.2.

Example 5

(±)-3-[1-(2-Ethoxyethyl)-trans-3,4-dimethylpiperidinyl]phenol

To a solution of (±)-3-(trans-3,4-dimethylpiperidinyl)phenol (60 mg, 0.29 mmol) in N,N-dimethylformamide (5.0 mL) at room temperature was added sodium hydrogencarbonate (27 mg, 0.32 mmol), and 2-bromoethyl ethyl ether (50 mg, 0.32 mmol). The solution was heated at 120° C. for 1 hour, cooled and then water (10 mL) was added. The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min⁻¹; employing U.V. detection at 275 nm; eluant gradient of acetonitrile:0.05 M aqueous ammonium acetate solution (90:10 to 10:90) to afford the title compound (31 mg, 39%) as its acetate salt.

¹H-NMR (data for the acetate salt): 0.82 (d, 3H), 1.18 (t, 3H), 1.30 (s, 3H), 1.70 (m, 1H), 2.01 (s, 3H), 2.05 (m, 1H), 2.38 (m, 1H), 2.81–3.05 (m, 5H), 3.20 (m, 1H), 3.42 (q, 2H), 3.68 (t, 2H), 6.65 (d, 1H), 6.72–6.80 (m, 2H), 7.12 (t, 1H). MS (TSI⁺): m/z [MH⁺] 278.5; $C_{17}H_{27}NO_2$+H requires 278.2.

Example 6

(±)-3-[1-(3-Tetrahydro-3-furanylpropyl)-trans-3,4-dimethylpiperidinyl]phenol

To a stirred solution of (±)-1-[trans-3,4-dimethyl-4-(3-hydroxyphenyl)piperidinyl]-3-(tetrahydro-3-furanyl)-1-propanone (Preparation 2, 150 mg, 0.47 mmol) in tetrahydrofuran (25 mL) at room temperature was added lithium aluminium hydride (2.2 mL, 1.0 M solution in diethyl ether). After 10 minutes, the reaction mixture was quenched with water and the resulting precipitate was removed by filtration through a pad of Celite®, washing with diethyl ether. The filtrate was dried over sodium sulfate, filtered and concentrated in vacuo to give the crude product (150 mg, 100%).

$^1$H-NMR: 0.77 (d, 3H), 1.27 (s, 3H), 1.32–1.61 (m, 6H), 1.92–2.03 (m, 2H), 2.18 (m, 1H), 2.22–2.41 (m, 4H), 2.46–2.58 (m, 2H), 2.82 (m, 1H), 3.30 (t, 1H), 3.73 (m, 1H), 3.81 (m, 1H), 3.88 (t, 1H), 6.59 (d, 1H), 6.71 (s, 1H), 6.80 (d, 1H), 7.10 (t, 1H). MS (TSI$^+$): m/z [MH$^+$] 318.5; $C_{20}H_{31}NO_2$+H requires 318.2.

Example 7

(±)-3-{1-[2-(2-Methoxyethoxy)ethyl]-trans-3,4-dimethylpiperidinyl}phenol

To a solution of (±)-3-(trans-3,4-dimethylpiperidinyl)phenol (60 mg, 0.29 mmol) in N,N-dimethylformamide (5.0 mL) at room temperature was added sodium hydrogencarbonate (27 mg, 0.32 mmol), and 1-bromo-2-(2-methoxyethoxy)ethane (59 mg, 0.32 mmol). The solution was heated at 120° C. for 1 hour, cooled and then water (10 mL) was added. The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound (71 mg, 80%) as its acetate salt.

$^1$H-NMR (data for the acetate salt): 0.82 (d, 3H), 1.35 (s, 3H), 1.72 (m, 1H), 2.03–2.10 (m, 4H), 2.38 (m, 1H), 2.81–3.13 (m, 6H), 3.40 (s, 3H), 3.50–3.63 (m, 4H), 3.70–3.78 (m, 2H), 6.68 (m, 1H), 6.81–6.82 (m, 2H), 7.18 (t, 1H). MS (TSI$^+$): m/z [MH$^+$] 308.3; $C_{18}H_{29}NO_3$+H requires 308.2.

Example 8

(±)-3-[1-(2-Methoxyethyl)-trans-3,4-dimethylpiperidinyl]phenol

To a solution of (±)-3-(trans-3,4-dimethylpiperidinyl)phenol (60 mg, 0.29 mmol) in N,N-dimethylformamide (5.0 mL) at room temperature was added sodium hydrogencarbonate (27 mg, 0.32 mmol), and 1-bromo-2-methoxyethane (45 mg, 0.32 mmol). The solution was heated at 120° C. for 1 hour, cooled and then added water (10 mL). The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound (17 mg, 22%) as its acetate salt.

$^1$H-NMR (data for the acetate salt): 0.83 (d, 3H), 1.35 (s, 3H), 1.72 (m, 1H), 2.03–2.09 (m, 4H), 2.38 (m, 1H), 2.70–3.18 (m, 6H), 3.38 (s, 3H), 3.58–3.65 (m, 2H), 6.68 (d, 1H), 6.79–6.84 (m, 2H), 7.18 (t, 1H). MS (TSI$^+$): m/z [MH$^+$] 264.2; $C_{16}H_{25}NO_2$+H requires 264.2.

Example 9

(±)-3-{1-[2-(Vinyloxy)ethyl]-trans-3,4-dimethylpiperidinyl}phenol

To a solution of (±)-3-(trans-3,4-dimethylpiperidinyl)phenol (60 mg, 0.29 mmol) in N,N-dimethylformamide (5.0 mL) at room temperature was 5 added sodium hydrogencarbonate (27 mg, 0.32 mmol), sodium iodide (48 mg, 0.32 mmol) and 2-chloroethyl vinyl ether (34 mg, 0.32 mmol). The solution was heated at 120° C. for 1 hour, cooled and then water (10 mL) was added. The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound (13 mg, 16%) as its acetate salt.

$^1$H-NMR (data for the acetate salt): 0.82 (d, 3H), 1.38 (s, 3H), 1.62 (m, 1H), 2.00–2.08 (m, 4H), 2.37 (m, 1H), 2.56–3.05 (m, 6H), 3.80–3.92 (m, 2H), 4.02 (d, 1H), 4.20 (d, 1H), 6.47 (dd, 1H), 6.65 (d, 1H), 6.79 (s, 1H), 6.85 (d, 1H), 7.18 (t, 1H). MS (TSI$^+$): m/z [MH$^+$] 276.3; $C_{17}H_{25}NO_2$+H requires 276.2.

Example 10

(±)-3-(1-{2-[2-(2-Hydroxyethoxy)ethoxy]ethyl}-trans-3,4-dimethylpiperidinyl)phenol To a solution of (±)-3-(trans-3,4-dimethylpiperidinyl)phenol (60 mg, 0.29 mmol) in N,N-dimethylformamide (5.0 mL) at room temperature was 25 added sodium hydrogencarbonate (27 mg, 0.32 mmol), sodium iodide (48 mg, 0.32 mmol) and 2-[2-(2-chloroethoxy)ethoxy]ethanol (54 mg, 0.32 mmol). The solution was heated at 120° C. for 1 hour, cooled and then water (10 mL) was added. The aqueous layer was extracted with ethyl acetate and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound (35 mg, 36%) as its acetate salt.

$^1$H-NMR (data for the acetate salt): 0.85 (d, 3H), 1.35 (s, 3H), 1.70 (m, 1H), 2.01–2.10 (m, 4H), 2.32 (m, 1H), 2.70–2.90 (m, 5H), 3.10 (m, 1H), 3.58–3.70 (m, 6H), 3.71–3.79 (m, 4H), 6.68 (d, 1H), 6.79–6.83 (m, 2H), 7.18 (t, 1H). MS (TSI$^+$): m/z [MH$^+$] 338.4; $C_{19}H_{31}NO_4$+H requires 338.2.

Example 11

(±)-3-{1-[3-(Tetrahydro-2H-pyran-2-yloxy)propyl]-trans-3,4-dimethylpiperidinyl}phenol To a solution of (±)-3-(trans-3,4-dimethylpiperidinyl)phenol (60 mg, 0.29 mmol) in N,N-dimethylformamide (5.0 mL) at room temperature was added sodium hydrogencarbonate (27 mg, 0.32 mmol), and 2-(3-bromopropoxy)tetrahydro-2H-pyran (71 mg, 0.32 mmol). The solution was heated at 120° C. for 1 hour, cooled and then water (10 mL)

was added. The aqueous layer was extracted with ethyl acetate and the combined organic layers were dried over sodium sulfate, and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound (39 mg, 39%) as its acetate salt.

$^1$H-NMR (data for the acetate salt): 0.85 (d, 3H), 1.35 (s, 3H), 1.47–1.92 (m, 9H), 2.01–2.10 (m, 4H), 2.38 (m, 1H), 2.56–2.80 (m, 5H), 3.01 (m, 1H), 3.40–3.56 (m, 2H), 3.78–3.90 (m, 2H), 4.58 (m, 1H), 6.64 (d, 1H), 6.79–6.83 (m, 2H), 7.18 (t, 1H). MS (TSI$^+$): m/z [MH$^+$] 348.2; $C_{21}H_{33}NO_3$+H requires 348.3.

Example 12

(±)-3-[1-(3-Tetrahydro-2H-pyran-2-ylpropyl)-trans-3,4-dimethylpiperidinyl]phenol To a stirred solution of 1-[trans-3,4-dimethyl-4-(3-hydroxyphenyl)piperidinyl]-3-(tetrahydro-2H-pyran-2-yl)-1-propanone (Preparation 3, 470 mg, 1.36 mmol) in diethyl ether (6.6 mL) at room temperature was added lithium aluminium hydride (1.0 M solution in diethyl ether, 2.72 mL, 2.72 mmol). After 2 hours the reaction was quenched by adding 2N aqueous sodium hydroxide (0.2 mL) followed by water (0.3 mL) and then diethyl ether (15 mL). The solid precipitate was then removed by filtration through a pad of Celite®, washing with ethyl acetate (5×50 mL). The filtrate was dried over sodium sulfate, filtered and concentrated in vacuo to give the title compound (396 mg, 88%) as a pale yellow oil.

$^1$H-NMR (selected data): 0.78 (d, 3H), 1.38 (s, 3H), 1.80 (m, 1H), 1.95 (m, 1H), 2.20–2.70 (m, 5H), 2.78–2.90 (m, 1H), 3.25 (m, 1H), 3.41 (m, 1H), 3.98 (m, 1H), 6.65 (d, 1H), 6.75 (s, 1H), 6.82 (d, 1H), 7.18 (t, 1H). MS (TSI$^+$): m/z [MH$^+$] 332.1; $C_{21}H_{33}NO_2$+H requires 332.3.

Example 13

(±)-3-{1-[3-(1,3-Dioxan-2-yl)propyl]-trans-3,4-dimethylpiperidinyl}phenol

To a solution of (±)-3-(trans-3,4-dimethylpiperidinyl)phenol (150 mg, 0.29 mmol) in N,N-dimethylformamide (4.0 mL) at room temperature was added sodium hydrogencarbonate (84 mg, 1.00 mmol), and 2-(3-bromopropyl)-1,3-dioxane (Preparation 4, 209 mg, 1.00 mmol). The solution was heated at 100° C. for 2 hours, cooled and then added to a mixture of saturated aqueous sodium hydrogencarbonate solution and diethyl ether (100 mL of 1:1). The aqueous layer was extracted with diethyl ether (2×50 mL) and the combined organic layers were washed with water (100 mL), dried over sodium sulfate, filtered and concentrated in vacuo to give a crude oil. This was purified by column chromatography on silica gel (10 g), eluting with $CH_2Cl_2$:ethanol:0.88 ammonia (100:8:1), to give the title compound (70 mg, 28%) as a white foam.

$^1$H-NMR: 0.78 (d, 3H), 1.35–1.70 (m, 9H), 1.90–2.18 (m, 2H), 2.23–2.64 (m, 6H), 2.85 (m, 1H), 3.68–3.79 (m, 2H), 4.02–4.18 (m, 2H), 4.52–4.57 (m, 1H), 6.61 (d, 1H), 6.70–6.80 (m, 2H), 7.15 (t, 1H).

Example 14

(±)-3-[1-(3,3-Dimethoxypropyl)-trans-3,4-dimethylpiperidinyl]phenol

To a solution of (±)-3-(trans-3,4-dimethylpiperidinyl)phenol (60 mg, 0.29 mmol) in N,N-dimethylformamide (2.5 mL) at room temperature was added sodium hydrogencarbonate (27 mg, 0.32 mmol), sodium iodide (48 mg, 0.32 mmol) and 3-chloro-1,1-dimethoxypropane (53 mg, 0.32 mmol) in N,N-dimethylformamide (2.0 mL). The mixture was heated at 120° C. for 1.5 hours, cooled and then water (30 mL) and ethyl acetate (10 mL) were added sequentially. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data from the acetate salt): 0.78 (d, 3H), 1.18–1.28 (m, 6H), 1.29 (s, 3H), 3.45–3.70 (m, 4H), 4.60 (t, 1H), 6.62 (dd, 1H), 6.72 (s, 1H), 6.82 (d, 1H), 7.18 (t, 1H). MS (APCI$^+$): m/z [MH$^+$] 336.2; $C_{20}H_{33}NO_3$+H requires 336.2.

Example 15

(±)-3-{1-[2-(2-Hydroxyethoxy)ethyl]-trans-3,4-dimethylpiperidinyl}phenol

To a solution of (±)-3-(trans-3,4-dimethylpiperidinyl)phenol (60 mg, 0.29 mmol) in N,N-dimethylformamide (2.5 mL) at room temperature was added sodium hydrogencarbonate (27 mg, 0.32 mmol), sodium iodide (48 mg, 0.32 mmol) and 2-(2-chloroethoxy)-1-ethanol (53 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (data from the acetate salt): 0.82 (d, 3H), 1.31 (s, 3H), 1.70 (m, 1H), 2.02 (s, 3H), 2.04 (m, 1H), 2.32 (m, 1H), 2.62–2.90 (m, 5H), 3.05 (m, 1H), 3.52–3.80 (m, 6H), 6.66 (dd, 1H), 6.72–6.80 (m, 2H), 7.15 (t, 1H). MS (APCI$^+$): m/z [MH$^+$] 294.1; $C_{17}H_{27}NO_3$+H requires 294.2.

Example 16

(±)-3-{1-[2-(1,3-Dioxolan-2-yl)ethyl]-trans-3,4-dimethylpiperidinyl}phenol

To a solution of (±)-3-(trans-3,4-dimethylpiperidinyl)phenol (60 mg, 0.29 mmol) in N,N-dimethylformamide (2.5 mL) at room temperature was added sodium hydrogencarbonate (27 mg, 0.32 mmol), and 2-(2-bromoethyl)-1,3-dioxolane (60 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data from the acetate salt): 0.80 (d, 3H), 1.30 (s, 3H), 1.65 (m, 1H), 1.90–1.97 (m, 2H), 2.02 (m, 1H), 2.35 (m, 1H), 2.43–2.70 (m, 5H), 2.90 (m, 1H), 3.80–3.98 (m, 4H), 4.93 (m, 1H), 6.66 (dd, 1H), 6.72–6.82 (m, 2H), 7.15 (t, 1H). MS (APCI$^+$): m/z [MH$^+$] 306.3; $C_{18}H_{27}NO_3$+H requires 306.2.

Example 17

(±)-3-{1-[4-(1,3-Dioxolan-2-yl)butyl]-trans-3,4-dimethylpiperidinyl}phenol

To a solution of (±)-3-(trans-3,4-dimethylpiperidinyl) phenol (60 mg, 0.29 mmol) in N,N-dimethylformamide (2.5 mL) at room temperature was added sodium hydrogencarbonate (27 mg, 0.32 mmol), sodium iodide (48 mg, 0.32 mmol) and 2-(4-chlorobutyl)-1,3-dioxolane (53 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data from the acetate salt): 0.81 (d, 3H), 1.38–1.70 (m, 7H), 2.03 (m, 1H), 2.36 (m, 1H), 2.43–2.78 (m, 5H), 2.98 (m, 1H), 3.80–3.98 (m, 4H), 4.93 (m, 1H), 6.66 (dd, 1H), 6.72–6.82 (m, 2H), 7.15 (t, 1H). MS (APCI$^+$): m/z [MH$^+$] 334.1; $C_{20}H_{31}NO_3$+H requires 334.2.

Example 18

(±)-3-{1-[2-(2,5,5-Trimethyl-1,3-dioxan-2-yl)ethyl]-trans-3,4-dimethylpiperidinyl}phenol To a solution of (±)-3-(trans-3,4-dimethylpiperidinyl) phenol (60 mg, 0.29 mmol) in N,N-dimethylformamide (2.5 mL) at room temperature was added sodium hydrogencarbonate (27 mg, 0.32 mmol), and 2-(2-bromoethyl)-2,5,5-trimethyl-1,3-dioxane (76 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data for the free base): 0.70 (s, 3H), 0.81 (d, 3H), 1.18 (s, 3H), 1.30 (s, 3H), 1.58–1.60 (m, 5H), 3.40 (d, 2H), 3.60 (d, 3H), 6.65 (m, 1H), 6.72–6.82 (m, 2H), 7.15 (t, 1H). MS (APCI$^+$): m/z [MH$^+$] 362.1; $C_{22}H_{35}NO_3$+H requires 362.3.

Example 19

(±)-3-{1-[2-(Tetrahydro-2H-pyran-2-yloxy)ethyl]-trans-3,4-dimethylpiperidinyl}phenol To a solution of (±)-3-(trans-3,4-dimethylpiperidinyl) phenol (60 mg, 0.29 mmol) in N,N-dimethylformamide (2.5 mL) at room temperature was added sodium hydrogencarbonate (27 mg, 0.32 mmol), sodium iodide (48 mg, 0.32 mmol) and 2-chloroethyl tetrahydro-2H-pyran-2-yl ether (52 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data from the acetate salt): 0.81 (d, 3H), 1.30 (s, 3H), 1.40–1.92 (m, 7H), 2.01–2.10 (m, 1H), 2.35 (m, 1H), 2.50–2.82 (m, 5H), 2.98 (m, 1H), 3.42–3.62 (m, 2H), 3.82–3.95 (m, 2H), 4.60 (m, 1H), 6.64 (d, 1H), 6.70–6.83 (m, 2H), 7.15 (t, 1H). MS (APCI$^+$): m/z [MH$^+$] 334.4; $C_{20}H_{31}NO_3$+H requires 334.2.

Example 20

(±)-3-[1-(5-Hydroxypentyl)-trans-3,4-dimethylpiperidinyl]phenol

To a solution of (±)-3-(trans-3,4-dimethylpiperidinyl) phenol (60 mg, 0.29 mmol) in N,N-dimethylformamide (2.5 mL) at room temperature was added sodium hydrogencarbonate (27 mg, 0.32 mmol), sodium iodide (48 mg, 0.32 mmol) and 5-chloro-1-pentanol (40 mg, 0.32 mmol) in N,N-dimethylformamide (2.0 mL). The mixture was heated at 120° C. for 1.5 hours, cooled and then water (30 mL) and ethyl acetate (10 mL) were added. The two layers were separated and the aqueous layer was extracted with ethyl acetate (2×10 mL) and the combined organic layers were dried over sodium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (selected data from the acetate salt): 0.78 (d, 3H), 1.31 (s, 3H), 1.38–1.70 (m, 7H), 2.84 (m, 1H), 3.65 (t, 2H), 6.61 (d, 1H), 6.75 (s, 1H), 6.83 (d, 1H), 7.15 (t, 1H). MS (APCI$^+$): m/z [MH$^+$] 291.9; $C_{18}H_{29}NO_2$+H requires 292.2.

Example 21

(±)-3-[1-(3-Tetrahydro-2H-pyran4-ylpropyl)-trans-3,4-dimethylpiperidinyl]phenol

To a stirred solution of (±)-1-[trans-3,4-dimethyl-4-(3-hydroxyphenyl)piperidinyl]-3-(tetrahydro-2H-pyran-4-yl)-1-propanone (Preparation 5, 500 mg, 1.45 mmol) in tetrahydrofuran (6 mL) at room temperature was added lithium aluminium hydride (1.0 M solution in diethyl ether, 2.72 mL, 2.72 mmol). After 1 hour, the reaction was quenched first with 2N aqueous sodium hydroxide (0.2 mL) and then water (0.3 mL) and diluted with diethyl ether (25 mL). The solid precipitate was then removed by filtration through a pad of Celite®, washing with ethyl acetate (5×50 mL). The filtrate was dried over magnesium sulfate, filtered and concentrated in vacuo to give the title compound (253 mg, 53%) as a white foam.

$^1$H-NMR (CD$_3$OD, selected data for the hydrochloride salt): 0.82 (d, 3H), 1.45 (s, 3H), 3.90–3.99 (m, 2H), 6.65 (d, 1H), 6.72 (s, 1H), 6.73 (d, 1H), 7.18 (t, 1H). MS (TSI$^+$): m/z [MH$^+$] 331.9; C$_{21}$H$_{33}$NO$_2$+H requires 332.3.

Example 22

(±)-3-{1-[2-(2-Naphthyloxy)ethyl]-trans-3,4-dimethylpiperidinyl}phenol

To a solution of (±)-3-(trans-3,4-dimethylpiperidinyl) phenol (82 mg, 0.40 mmol) in N,N-dimethylformamide (2.0 mL) at room temperature was added sodium hydrogencarbonate (35 mg, 0.42 mmol), and 2-(2-iodoethoxy) naphthalene (Preparation 11, 120 mg, 0.40 mmol). The mixture was heated at 150° C. for 2 hours, and then at room temperature for 16 hours. The solution was then partitioned between water (5 mL) and diethyl ether (10 mL). The two layers were separated and the aqueous layer was extracted with diethyl ether (1×10 mL) and the combined organic layers were dried over sodium sulfate, filtered and concentrated in vacuo to give a crude oil. This was purified using a Waters Sep-Pak™ cartridge packed with silica gel (10 g), eluting with a gradient of CH$_2$Cl$_2$:EtOH:0.88 ammonia (100:0:0 to 500:20:1), to give the title compound (64 mg, 43%) as a brown solid.

$^1$H-NMR: 0.82 (d, 3H), 1.38 (s, 3H), 1.62 (m, 1H), 2.02 (m, 1H), 2.37 (m, 1H), 2.50–3.10 (m, 6H), 4.20–4.30 (m, 2H), 6.64 (d, 1H), 6.78 (s, 1H), 6.85 (d, 1H), 7.10–7.22 (m, 3H), 7.36 (t, 1H), 7.45 (t, 1H), 7.70–7.80 (m, 3H). MS (TSI$^+$): m/z [MH$^+$] 376.7; C$_{25}$H$_{29}$NO$_2$+H requires 376.2.

Example 23

(±)-3-[1-(2-Isopropoxyethyl)-trans-3,4-dimethylpiperidinyl]phenol

To a solution of (±)-3-(trans-3,4-dimethylpiperidinyl) phenol (82 mg, 0.40 mmol) in N,N-dimethylformamide (2.0 mL) at room temperature was added sodium hydrogencarbonate (35 mg, 0.42 mmol), and 2-(2-iodoethoxy)propane (Preparation 13, 86 mg, 0.40 mmol). The mixture was heated at 150° C. for 2 hours, and then at room temperature for 16 hours. The reaction mixture was partitioned between water (20 mL) and diethyl ether (20 mL). The two layers were separated and the aqueous layer was extracted with diethyl ether (1×20 mL) and the combined organic layers were dried over sodium sulfate, filtered and concentrated in vacuo to give a crude oil. This was purified using a Waters Sep-Pak™ cartridge packed with silica gel (10 g), eluting with a gradient of CH$_2$Cl$_2$: EtOH:0.88 ammonia (100:0:0 to 500:20:1), to give the title compound (59 mg, 51%) as a brown oil.

$^1$H-NMR: 0.80 (d, 3H), 1.18 (d, 6H), 1.35 (s, 3H), 1.60 (m, 1H), 2.02 (m, 1H), 2.37 (m, 1H), 2.40–2.90 (m, 6H), 3.55–3.65 (m, 3H), 6.64 (d, 1H), 6.78 (s, 1H), 6.85 (d, 1H), 7.18 (t, 1H). MS (TSI$^+$): m/z [MH$^+$] 292.3; C$_{18}$H$_{29}$NO$_2$+H requires 292.2.

Example 24

3-[1-(2-Propoxyethyl)-trans-3,4-dimethylpiperidinyl]phenol

To a solution of (±)-3-(trans-3,4-dimethylpiperidinyl) phenol (82 mg, 0.40 mmol) in N,N-dimethylformamide (2.0 mL) at room temperature was added sodium hydrogencarbonate (35 mg, 0.42 mmol), and 1-(2-iodoethoxy)propane (Preparation 15, 86 mg, 0.40 mmol). The mixture was heated at 150° C. for 2 hours, and then at room temperature for 16 hours. The reaction mixture was partitioned between water (20 mL) and diethyl ether (20 mL). The two layers were separated and the aqueous layer was extracted with diethyl ether (1×20 mL) and the combined organic layers were dried over sodium sulfate, filtered and concentrated in vacuo to give a crude oil. This was purified using a Waters Sep-Pak™ cartridge packed with silica gel (10 g), eluting with dichloromethane:ethanol:0.88 ammonia (500:20:1), to give the title compound (43 mg, 37%) as a brown oil.

$^1$H-NMR (selected data): 0.88–0.95 (m, 3H), 0.95 (t, 3H), 1.32 (s, 3H), 3.41 (t, 2H), 3.50–3.64 (m, 2H), 6.66 (d, 1H), 6.78 (s, 1H), 6.85 (d, 1H), 7.18 (t, 1H). MS (APCI$^+$): m/z [MH$^+$] 292.0; C$_{18}$H$_{29}$NO$_2$+H requires 292.2.

Example 25

(±)-3-{1-[2-(Cyclopentyloxy)ethyl]-trans-3,4-dimethylpiperidinyl}phenol

To a solution of (±)-3-(trans-3,4-dimethylpiperidinyl) phenol (21 mg, 0.10 mmol) in N,N-dimethylformamide (2.0 mL) at room temperature was added sodium hydrogencarbonate (10 mg, 0.12 mmol), and 1-(2-iodoethoxy) cyclopentane (Preparation 17, 15 mg, 0.06 mmol). The mixture was heated at 150° C. for 2 hours, and then at room temperature for 16 hours. The reaction mixture was partitioned between water (8 mL) and diethyl ether (15 mL). The two layers were separated and the aqueous layer was extracted with diethyl ether (1×15 mL) and the combined organic layers were dried over sodium sulfate, filtered and concentrated in vacuo to give a crude oil. This was purified using a Waters Sep-Pak™ cartridge packed with silica gel (5 g), eluting with a gradient of CH$_2$Cl$_2$:EtOH:0.88 ammonia (100:0:0 to 500:20:1), to give the title compound (15 mg, 47%) as a brown oil.

$^1$H-NMR: 0.78 (d, 3H), 1.30 (s, 3H), 1.40–1.80 (m, 9H), 1.98 (m, 1H), 2.35 (m, 1H), 2.42–2.50 (m, 5H), 2.86 (m, 1H), 3.56 (t, 2H), 3.90 (m, 1H), 6.64 (d, 1H), 6.78 (s, 1H), 6.83 (d, 1H), 7.18 (t, 1H). MS (TSI$^+$): m/z [MH$^+$] 318.1; C$_{20}$H$_{31}$NO$_2$+H requires 318.2.

Example 26

(±)-3-[1-(3-Tetrahydro-2-furanylpropyl)-trans-3,4-dimethylpiperidinyl]phenol

To a stirred solution of (±)-1-[trans-3,4-dimethyl-4-(3-hydroxyphenyl)piperidinyl]-3-(tetrahydro-2-furanyl)-1-propanone (Preparation 6, 270 mg, 0.82 mmol) in tetrahydrofuran (25 mL) at room temperature was added lithium aluminium hydride (1.0 M solution in diethyl ether, 4.0 mL, 4.0 mmol). After 10 minutes at room temperature the reaction was quenched with water. The aqueous layer was extracted with ethyl acetate, dried over magnesium sulfate, filtered and concentrated in vacuo to give the title compound (170 mg, 67%) as a brown oil.

$^1$H-NMR: 0.80 (d, 3H), 1.30 (s, 3H), 1.40–2.05 (m, 10H), 2.25–2.70 (m, 6H), 2.85 (m, 1H), 3.65–3.90 (m, 3H), 6.64 (d, 1H), 6.78 (s, 1H), 6.83 (d, 1H), 7.18 (t, 1H). MS (TSI$^+$): m/z [MH$^+$] 318.3; C$_{20}$H$_{31}$NO$_2$+H requires 318.2.

Example 27

(±)-3-{1-[2-(Cyclohexylsulfanyl)ethyl]-trans-3,4-dimethylpiperidinyl}phenol

To a solution of (±)-3-(trans-3,4-dimethylpiperidinyl) phenol (150 mg, 0.29 mmol) in N,N-dimethylformamide (10 mL) at room temperature was added sodium hydrogencarbonate (70 mg, 0.80 mmol), sodium iodide (120 mg, 0.80 mmol) and 1-[(2-chloroethyl)sulfanyl]cyclohexane (140 mg, 0.80 mmol). The mixture was heated at reflux for 1 hour, cooled and then water and ethyl acetate were added. The two layers were separated and the aqueous layer was extracted with ethyl acetate and the combined organic layers were dried over magnesium sulfate, filtered and concentrated in vacuo to give a crude oil. This was purified by preparative HPLC on a Dynamax™ column, 42×250 mm; flow 8.0 mL min$^{-1}$; employing U.V. detection at 275 nm; eluant gradient of acetonitrile:0.05 M aqueous ammonium acetate solution (90:10 to 10:90) to afford the title compound as its acetate salt.

$^1$H-NMR (data for the free base): 0.79 (d, 3H), 1.20–1.40 (m, 9H), 1.60–2.00 (m, 6H), 2.24–2.95 (m, 10H), 6.60 (d, 1H), 6.70 (s, 1H), 6.80 (d, 1H), 7.12 (t, 1H). MS (TSI$^+$): m/z [MH$^+$] 348.2; $C_{21}H_{33}NOS+H$ requires 348.2.

Example 28

(±)-3-{1-[2-(Ethylsulfanyl)ethyl]-trans-3,4-dimethylpiperidinyl}phenol

To a solution of (±)-3-(trans-3,4-dimethylpiperidinyl)phenol (100 mg, 0.49 mmol) in N,N-dimethylformamide (2 mL) at room temperature was added sodium hydrogencarbonate (47 mg, 0.56 mmol), sodium iodide (7 mg, 0.05 mmol) and 2-chloroethyl ethyl sulfide (70 mL, 0.56 mmol). The mixture was heated at 140° C. for 1 hour, cooled and then concentrated in vacuo to give a crude oil. This was purified by column chromatography on silica gel (10 g), eluting with a gradient of dichloromethane:ethanol:0.88 ammonia (500:8:1 to 300:8:1), to give the title compound (120 mg, 83%) as an orange oil.

$^1$H-NMR: 0.77 (d, 3H), 1.20 (t, 3H), 1.26 (s, 3H), 1.57 (m, 1H), 1.95 (m, 1H), 2.26 (m, 1H), 2.38 (m, 1H), 2.50–2.68 (m, 8H), 2.81 (m, 1H), 6.59 (d, 1H), 6.71 (s, 1H), 6.81 (d, 1H), 7.12 (t, 1H). MS (APCI$^+$): m/z [MH$^+$] 294.4; $C_{17}H_{27}NOS+H$ requires 294.2.

Example 29

(±)-3-{1-[2-(Ethylsulfinyl)ethyl]-trans-3,4-dimethylpiperidinyl}phenol

To a solution of (±)-3-(trans-3,4-dimethylpiperidinyl)phenol (100 mg, 0.49 mmol) in N,N-dimethylformamide (2 mL) at room temperature was added sodium hydrogencarbonate (47 mg, 0.56 mmol), sodium iodide (7 mg, 0.05 mmol) and 2-chloroethyl ethyl sulfoxide (Preparation 7, 76 mg, 0.54 mmol). The mixture was heated at reflux for 1.5 hours, cooled and then concentrated in vacuo to give a crude oil. This was purified by column chromatography on silica gel (10 g), eluting with dichloromethane:ethanol:0.88 ammonia (200:8:1), to give the title compound (43 mg, 28%) as a brown solid.

$^1$H-NMR: 0.70–0.80 (m, 3H), 1.26 (s, 3H), 1.28–1.38 (m, 3H), 1.58 (m, 1H), 1.95 (m, 1H), 2.18–2.90 (m, 1H), 6.61 (d, 1H), 6.71–6.80 (m, 2H), 7.12 (t, 1H). MS (APCI$^+$): m/z [MH$^+$] 310.5; $C_{17}H_{27}NO_2S+H$ requires 310.2.

Example 30

(±)-3-{1-[2-(Ethylsulfonyl)ethyl]-trans-3,4-dimethylpiperidinyl}phenol

To a solution of (±)-3-(trans-3,4-dimethylpiperidinyl)phenol (100 mg, 0.49 mmol) in N,N-dimethylformamide (2 mL) at room temperature was added sodium hydrogencarbonate (47 mg, 0.56 mmol), sodium iodide (7 mg, 0.05 mmol) and 2-chloroethyl ethyl sulfone (Preparation 8, 88 mg, 0.56 mmol). The mixture was heated at 140° C. for 1 hour, cooled and then concentrated in vacuo to give a crude oil. This was purified by column chromatography on silica gel (10 g), eluting with $CH_2Cl_2$:EtOH:0.88 ammonia (500:8:1), to give the title compound (155 mg, 97%) as an orange oil.

$^1$H-NMR: 0.70 (m, 3H), 1.27 (s, 3H), 1.35 (t, 3H), 1.59 (m, 1H), 1.96 (m, 1H), 2.22 (m, 1H), 2.38 (m, 1H), 2.47–2.63 (m, 2H), 2.79–2.85 (m, 3H), 2.99–3.18 (m, 4H), 6.61 (d, 1H), 6.72 (s, 1H), 6.80 (d, 1H), 7.15 (t, 1H). MS (APCI$^+$): m/z [MH$^+$] 326.4; $C_{17}H_{27}NO_3S+H$ requires 326.2.

Example 31

(±)-3-{1-[3-(1H-1,2,3,4-Tetrazol-1-yl)propyl]-trans-3,4-dimethylpiperidinyl}phenol To a solution of (±)-3-[1-(3-hydroxypropyl)-trans-3,4-dimethylpiperidinyl]phenol (Example 3, 155 mg, 0.59 mmol), 1H-tetrazole (42 mg, 0.60 mmol) and triphenylphosphine (155 mg, 0.59 mmol) in dichloromethane (2 mL) at 0° C. was added diethyl azodicarboxylate (103 mg, 0.59 mmol) dropwise via syringe. The reaction was stirred at room temperature for 16 hours, and then treated with more triphenylphosphine (75 mg, 0.29 mmol) and diethyl azodicarboxylate (51 mg, 0.29 mmol). After stirring at room temperature for a further 16 hours the reaction was concentrated in vacuo to give a crude residue. This was purified by column chromatography on silica gel (20 g), eluting with a gradient of dichloromethane:ethanol:0.88 ammonia (300:8:1 to 200:8:1), to give the title compound (53 mg, 29%) as an oil.

$^1$H-NMR: 0.80 (m, 3H), 1.32 (s, 3H), 1.59 (m, 1H), 2.00 (m, 1H), 2.15–2.60 (m, 8H), 2.81 (m, 1H), 4.75 (t, 2H), 6.65 (dd, 1H), 6.76 (s, 1H), 6.85 (d, 1H), 7.18 (t, 1H), 8.50 (s, 1H). MS (APCI$^+$) m/z [MH$^+$] 316.5; $C_{17}H_{25}N_5O+H$ requires 316.2.

Example 32

(±)-3-{1-[3-(1H-Pyrazol-1-yl)propyl]-trans-3,4-dimethylpiperidinyl}phenol

To a stirred solution of (±)-1-[trans-3,4-dimethyl-4-(3-hydroxyphenyl)piperidinyl]-3-(1H-pyrazol-1-yl)-1-propanone (Preparation 9, 71 mg, 0.22 mmol) in tetrahydrofuran (3 mL) at room temperature was added lithium aluminium hydride (1.0 M solution in diethyl ether, 0.4 mL, 0.4 mmol). After 10 minutes at room temperature the reaction was quenched with water and diluted with ethyl acetate. The solid precipitate was removed by filtration through a pad of Celite®, and brine was added to the filtrate. The two layers were separated and the organic layer was dried over magnesium sulfate, filtered and concentrated in vacuo to give the title compound (49 mg, 71%) as an oil.

$^1$H-NMR (CD$_3$OD, selected data): 0.80 (d, 3H), 1.38 (s, 3H), 6.32 (s, 1H), 6.61 (d, 1H), 6.68 (s, 1H), 6.72 (d, 1H), 7.15 (t, 1H), 7.58 (s, 1H), 7.70 (s, 1H). MS (TSI$^+$): m/z [MH$^+$] 314.3; $C_{19}H_{27}N_3O+H$ requires 314.2.

Example 33

(±)-3-{1-[3-(4-Pyridinyl)propyl]-trans-3,4-dimethylpiperidinyl}phenol

To a solution of 4-pyridinepropanol (1.0 g, 7.29 mmol) in dichloromethane (25 mL) at 0° C. was added methanesulfonyl chloride (0.90 g, 7.90 mmol). The mixture was stirred at room temperature for 1 hour and was then concentrated in vacuo. This crude oil was dissolved in 1,2-dimethoxyethane (10 mL) and then added to a solution of (±)-3-(trans-3,4-dimethylpiperidinyl)phenol (300 mg, 1.46 mmol) and sodium hydrogencarbonate (1.0 g, 11.9 mmol). The mixture was heated at reflux for 16 hours, cooled and then filtered. The filtrate was concentrated in vacuo to give a crude residue which was purified by column chromatography on silica gel, eluting with a gradient of dichloromethane:methanol (98:2 to 0:100). This gave the title compound as a pale brown solid.

$^1$H-NMR (D$_2$O, selected data for the HCl salt): 0.70 (d, 3H), 1.30 (s, 3H), 6.70 (d, 1H), 6.78 (s, 1H), 6.88 (d, 1H), 7.20 (t, 1H), 7.22–7.25 (m, 2H), 8.29–8.35 (m, 2H). MS (TSI$^+$): m/z [MH$^+$] 325.5; C$_{21}$H$_{28}$N$_2$O+H requires 325.2.

Example 34

(±)-3-{1-[3-(1H-1,2,4-Triazol-1-yl)propyl]-trans-3,4-dimethylpiperidinyl}phenol

To a solution of (±)-3-(trans-3,4-dimethylpiperidinyl)phenol (150 mg, 0.73 mmol) in N,N-dimethylformamide (6 mL) at room temperature was added sodium hydrogencarbonate (62 mg, 0.80 mmol), and 1-(3-bromopropyl)-1H-1,2,4-triazole (prepared as described in DE 4115433 A1: 152 mg, 0.80 mmol). The mixture was heated at reflux for 1.5 hours, and then at room temperature for 16 hours. The solution was then poured into water (100 mL) and made basic (pH 9) with 2N aqueous sodium hydroxide solution. The aqueous layer was extracted with diethyl ether (2×100 mL) and the combined organic layers were dried over magnesium sulfate, filtered and concentrated in vacuo to give a crude oil. This was purified using a Waters Sep-Pak™ cartridge packed with silica gel (10 g), eluting with dichloromethane:ethanol:0.88 ammonia (200:8:1), to give the title compound (130 mg, 57%) as a yellow oil.

$^1$H-NMR: 0.80 (m, 3H), 1.30 (s, 3H), 1.59 (m, 1H), 1.95–2.38 (m, 7H), 2.48–2.58 (m, 2H), 2.78 (m, 1H), 4.26 (t, 2H), 6.62 (m, 1H), 6.78 (m, 1H), 6.84 (d, 1H), 7.15 (t, 1H), 7.95 (s, 1H), 8.05 (s, 1H). MS (TSI$^+$): m/z [MH$^+$] 315.6; C$_{18}$H$_{26}$N$_4$O+H requires 315.2.

Example 35

(±)-3-{1-[3-(1H-Pyrrol-1-yl)propyl]-trans-3,4-dimethylpiperidinyl}phenol

To a solution of (±)-3-(trans-3,4-dimethylpiperidinyl)phenol (60 mg, 0.29 mmol) in acetonitrile (2.5 mL) at room temperature was added sodium hydrogencarbonate (27 mg, 0.32 mmol), and 1-(3-bromopropyl)-1H-pyrrole (43 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR (selected data): 0.81 (d, 3H), 1.28 (s, 3H), 3.98 (t, 3H), 6.05–6.15 (m, 2H), 6.60–6.69 (m, 3H), 6.78 (s, 1H), 6.85 (d, 1H), 7.18 (t, 1H). MS (APCI$^+$): m/z [MH$^+$] 313.1; C$_{20}$H$_{28}$N$_2$O+H requires 313.2.

Example 36

(±)-3-[trans-3,4-Dimethyl-4-(3-hydroxyphenyl)piperidinyl]-1-(4-morpholinyl)-1-propanone To a solution of 4-acryloylmorpholine (152 mg, 1.08 mmol) in tetrahydrofuran (4 mL) at room temperature was added (±)-3-(trans-3,4-dimethylpiperidinyl)phenol (200 mg, 0.97 mmol). The mixture was heated at reflux for 16 hours and then cooled. The solvent was removed in vacuo to give a pale yellow oil. This was purified by column chromatography, eluting with a gradient of CH$_2$Cl$_2$:EtOH:0.88 ammonia (300:8:1 to 100:8:1), to give the title compound (327 mg, 97%) as a white solid.

$^1$H-NMR: 0.72 (d, 3H), 1.27 (s, 3H), 1.58 (m, 1H), 1.95 (m, 1H), 2.20–2.85 (m, 9H), 3.42–3.48 (m, 2H), 3.52–3.62 (m, 6H), 6.60 (m, 1H), 6.73 (s, 1H), 6.79 (d, 1H), 7.12 (t, 1H). MS (TSI$^+$): m/z [MH$^+$] 347.4; C$_{20}$H$_{30}$N$_2$O$_3$+H requires 347.2.

Example 37

3-{1-[3-(4-Morpholinyl)propyl]-trans-3,4-dimethylpiperidinyl}phenol

To a stirred solution of (±)-3-[trans-3,4-dimethyl-4-(3-hydroxyphenyl)piperidinyl]-1-(4-morpholinyl)-1-propanone (Example 36, 150 mg, 0.43 mmol) in tetrahydrofuran (3 mL) at 0° C. was added lithium aluminium hydride (1.0 M solution in diethyl ether, 0.47 mL, 0.47 mmol). After 15 minutes at 0° C. the mixture was warmed to room temperature and stirred at ambient temperature for 16 hours. The reaction was quenched with a saturated ammonium chloride solution (5 mL) and water (5 mL). The aqueous layer was extracted with ethyl acetate (4×10 mL) and the combined organic layers were dried over sodium sulfate, filtered and concentrated in vacuo to give a yellow oil. This was purified by column chromatography on silica gel (7.5 g), eluting with dichloromethane:ethanol:0.88 ammonia (100:8:1), to give the title compound (124 mg, 87%) as a pale yellow oil.

$^1$H-NMR: 0.75 (d, 3H), 1.26 (s, 3H), 1.57 (m, 1H), 1.62–1.70 (m, 2H), 1.98 (m, 1H), 2.25–2.59 (m, 12H), 2.80 (m, 1H), 3.67–3.71 (m, 4H), 6.59 (m, 1H), 6.72 (s, 1H), 6.78 (d, 1H), 7.12 (t, 1H). MS (APCI$^+$): m/z [MH$^+$] 333.1; C$_{20}$H$_{32}$N$_2$O$_2$+H requires 333.3.

Example 38

3-{1-[2-(1-Azepanyl)ethyl]-trans-3,4-dimethylpiperidinyl}phenol

To a solution of (±)-3-(trans-3,4-dimethylpiperidinyl)phenol (60 mg, 0.29 mmol) in acetonitrile (2.5 mL) at room temperature was added sodium hydrogencarbonate (27 mg, 0.32 mmol), sodium iodide (48 mg, 0.32 mmol) and a mixture of 1-(2-chloroethyl)azepane hydrochloride (64 mg, 0.32 mmol) and triethylamine (32 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR: 0.78 (d, 3H), 1.28 (s, 3H), 1.56–1.78 (m, 9H), 1.97 (m, 1H), 2.20–2.43 (m, 2H), 2.56–2.98 (m, 1H), 6.67 (m, 1H), 6.72–6.81 (m, 2H), 7.15 (t, 1H). MS (APCI$^+$): m/z [MH$^+$] 331.1; C$_{21}$H$_{34}$N$_2$O+H requires 331.3.

Example 39

3-{1-[2-(4-Morpholinyl)ethyl]-trans-3,4-dimethylpiperidinyl}phenol

To a solution of (±)-3-(trans-3,4-dimethylpiperidinyl)phenol (60 mg, 0.29 mmol) in acetonitrile (2.5 mL) at room temperature was added sodium hydrogencarbonate (27 mg, 0.32 mmol), sodium iodide (48 mg, 0.32 mmol) and a mixture of 4-(2-chloroethyl)morpholine hydrochloride (60 mg, 0.32 mmol) and triethylamine (32 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR: 0.82 (d, 3H), 1.35 (s, 3H), 1.72 (m, 1H), 2.10 (m, 1H), 2.33–2.86 (m, 12H), 2.98 (m, 1H), 3.68–3.77 (m, 4H), 6.67 (m, 1H), 6.78 (s, 1H), 6.84 (d, 1H), 7.15 (t, 1H). MS (APCI$^+$): m/z [MH$^+$] 319.2; $C_{19}H_{30}N_2O_2$+H requires 319.2.

Example 40

3-{1-[2-(1-Piperidinyl)ethyl]-trans-3,4-dimethylpiperidinyl}phenol

To a solution of (±)-3-(trans-3,4-dimethylpiperidinyl) phenol (60 mg, 0.29 mmol) in acetonitrile (2.5 mL) at room temperature was added sodium hydrogencarbonate (27 mg, 0.32 mmol), sodium iodide (48 mg, 0.32 mmol) and a mixture of 1-(2-chloroethyl)piperidine hydrochloride (59 mg, 0.32 mmol) and triethylamine (32 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR: 0.79 (d, 3H), 1.29 (s, 3H), 1.40–1.80 (m, 7H), 2.01 (m, 1H), 2.20–2.90 (m, 13H), 6.65 (m, 1H), 6.75 (s, 1H), 6.80 (d, 1H), 7.15 (t, 1H). MS (APCI$^+$): m/z [MH$^+$] 317.1; $C_{20}H_{32}N_2O$+H requires 317.3.

Example 41

3-{1-[2-(1-Pyrrolidinyl)ethyl]-trans-3,4-dimethylpiperidinyl}phenol

To a solution of (±)-3-(trans-3,4-dimethylpiperidinyl) phenol (60 mg, 0.29 mmol) in acetonitrile (2.5 mL) at room temperature was added sodium hydrogencarbonate (27 mg, 0.32 mmol), sodium iodide (48 mg, 0.32 mmol) and a mixture of 1-(2-chloroethyl)pyrrolidine hydrochloride (54 mg, 0.32 mmol) and triethylamine (32 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR: 0.79 (d, 3H), 1.29 (s, 3H), 1.58 (m, 1H), 1.67–1.90 (m, 4H), 2.01 (m, 1H), 2.20–2.90 (m, 13H), 6.65 (m, 1H), 6.70 (s, 1H), 6.81 (d, 1H), 7.15 (t, 1H). MS (APCI$^+$): m/z [MH$^+$] 303.1; $C_{19}H_{30}N_2O$+H requires 303.2.

Example 42

3-{1-[3-(1-Piperidinyl)propyl]-trans-3,4-dimethylpiperidinyl}phenol

To a solution of (±)-3-(trans-3,4-dimethylpiperidinyl) phenol (60 mg, 0.29 mmol) in acetonitrile (2.5 mL) at room temperature was added sodium hydrogencarbonate (27 mg, 0.32 mmol), sodium iodide (48 mg, 0.32 mmol) and a mixture of 1-(3-chloropropyl)piperidine hydrochloride (63 mg, 0.32 mmol) and triethylamine (32 mg, 0.32 mmol) in acetonitrile (2.5 mL). The solution was heated at reflux for 3 hours, cooled and then water was added. The aqueous layer was extracted with ethyl acetate and the combined organic layers were dried over magnesium sulfate, filtered and concentrated in vacuo to give the title compound as an oil.

$^1$H-NMR: 0.80 (d, 3H), 1.25–2.01 (m, 13H), 2.20–2.95 (m, 13H), 6.65 (m, 1H), 6.72–6.81 (m, 2H), 7.15 (t, 1H). MS (APCI$^+$): m/z [MH$^+$] 331.2; $C_{21}H_{34}N_2O$+H requires 331.3.

Example 43

(±)-3-[1-(3-Methoxyphenyl)-trans-3,4-dimethylpiperidinyl]phenol

To a solution of (±)-3-(trans-3,4-dimethylpiperidinyl) phenol (82 mg, 0.40 mmol), 3-bromoanisole (56 μL, 0.44 mmol) and tri-o-tolylphosphine (5 mg, 0.04 mmol) in toluene (2 mL) was added sodium tert-butoxide (54 mg, 0.56 mmol) and tris(dibenzylideneacetone)-palladium(0) (8 mg, 0.02 mmol) and the reaction mixture was heated at reflux for 6 h. After cooling, the reaction mixture was concentrated in vacuo to give the crude product which was purified by column chromatography on silica gel, eluting with a gradient of methanol:dichloromethane:0.880 ammonia (10:990:1 to 30:970:3), to give the title compound (36 mg, 29%) as a yellow oil.

$^1$H-NMR ($C_6D_6$): 0.78 (d, 3H), 1.08 (s, 3H), 1.25 (m, 1H), 1.72 (m, 1H), 2.10 (m, 1H), 2.70 (m, 1H), 2.95 (m, 1H), 3.15 (m, 1H), 3.32 (m, 1H), 3.39 (s, 3H), 4.01 (br s, 1H), 6.34–6.40 (m, 2H), 6.52–6.55 (m, 2H), 6.64 (m, 1H), 6.67 (m, 1H), 7.01 (t, 1H), 7.15 (t, 1H). MS (APCI$^+$): m/z [MH$^+$] 312.1; $C_{20}H_{25}NO_2$+H requires 312.2.

Example 44

(±)-3-{1-[4-(Dimethylamino)phenyl]-trans-3,4-dimethylpiperidinyl}phenol

To a stirred solution of (±)-4-(3-hydroxyphenyl)-trans-3,4-dimethylpiperidine (82 mg, 0.40 mmol), N,N-dimethyl4-bromoaniline (112 mg, 0.56 mmol) and tri-o-tolylphosphine (5 mg, 0.04 mmol) in toluene (2 mL) was added sodium tert-butoxide (54 mg, 0.56 mmol) and tris (dibenzylideneacetone)palladium(0) (8 mg, 0.02 mmol) and the reaction mixture was heated at reflux for 48 hours. After cooling, the reaction mixture was diluted with water (20 mL) and extracted with dichloromethane (3×20 mL). The combined extracts were washed with brine (20 mL), dried over sodium sulfate, filtered and concentrated in vacuo to give the crude product. This was purified by column chromatography on silica gel, eluting with a gradient of methanol dichloromethane:0.88 ammonia (10:990:1 to 20:980:1), to give the title compound (23 mg, 18%) as a yellow oil.

$^1$H-NMR ($C_6D_6$): 0.91 (d, 3H), 1.16 (s, 3H), 1.32 (m, 1H), 1.74 (m, 1H), 2.12 (m, 1H), 2.44–2.58 (m, 6H), 2.75 (m, 1H), 3.03 (m, 2H), 3.21 (m, 1H), 6.57 (m, 1H), 6.69 (m, 1H), 6.71–6.76 (m, 3H), 6.83–6.92 (m, 2H), 7.07 (t, 1H). MS (APCI$^+$): m/z [MH$^+$] 325.2; $C_{21}H_{28}N_2O$+H requires 325.2.

Example 45

(±)-Methyl 3-[trans-3,4-Dimethyl-4-(3-hydroxyphenyl)piperidinyl]propionate

To a stirred solution of (±)-3-(trans-3,4-dimethylpiperidinyl)phenol (82 mg, 0.40 mmol) in methanol (3 mL) at room temperature was added methyl acrylate (54 μL, 0.6 mmol). After 2 hours at room temperature the reaction mixture was concentrated in vacuo to give the crude product. This was purified by column chromatography on silica gel, eluting with a gradient of methanol:dichloromethane:0.880 ammonia (10:990:1 to 30:970:3), to give the title compound (60 mg, 51%) as a pale yellow oil.

$^1$H-NMR ($C_6D_6$, data for the free base): 0.82 (d, 3H), 1.13 (s, 3H), 1.32 (m, 1H), 1.73 (m, 1H), 2.09 (m, 1H), 2.17–2.35 (m, 5H), 2.46–2.59 (m, 3H), 3.29 (s, 3H), 5.90 (br s, 1H), 6.63 (dd, 1H), 6.69 (d, 1H), 6.76 (m, 1H), 7.06 (m, 1H). MS (APCI$^+$): m/z [MH$^+$] 292.3; $C_{17}H_{25}NO_3$+H requires 292.2.

Example 46

Compounds according to the present invention, for example the compound of Example 5, were found to display anti-pruritic activity when tested in accordance with the above procedure. PREPARATION OF STARTING MATERIALS Preparation 1

3-(Tetrahydro-3-furanyl)propionic Acid

To a solution of trans-3-furanacrylic acid (10 g, 72.4 mmol) in industrial methylated spirits (50 mL) was added 10% palladium on carbon (1.0 g) at room temperature. The reaction vessel was charged with hydrogen gas to a pressure of 345 kPa and stirred at room temperature for 16 hours. The catalyst was removed by filtration and the filtrate was concentrated in vacuo to give the title compound as a colourless oil.

$^1$H-NMR: 1.44–1.58 (m, 1H), 1.61–1.82 (m, 2H), 1.99–2.12 (m, 1H), 2.15–2.48 (m, 3H), 3.38 (t, 1H), 3.62–3.98 (m, 3H).

Preparation 2

(±)-1-[trans-3,4-Dimethyl-4-(3-hydroxyphenyl) piperidinyl]-3-(tetrahydro-3-furanyl)-1-propanone To a solution of 3-(tetrahydro-3-furanyl)propionic acid (Preparation 1, 202 mg, 1.40 mmol) in N,N-dimethylformamide (40 mL) at room temperature was added 1-(3-dimethylaminopropyl)-3-ethylcarbodiimide hydrochloride (320 mg, 1.70 mmol) and 1-hydroxybenzotriazole (204 mg, 1.51 mmol). After the mixture had become homogeneous, (±)-3-(trans-3,4-dimethylpiperidinyl)phenol (300 mg, 1.46 mmol) was added in one portion. The mixture was stirred at room temperature for 16 hours and then water was added. The aqueous layer was extracted with diethyl ether and the combined organic layers were dried over sodium sulfate, filtered and concentrated in vacuo to give a crude clear residue. This was purified by column chromatography on silica gel, eluting with ethyl acetate, to give the title compound (150 mg, 30%) as a colourless oil.

$^1$H-NMR (5:4 mixture of rotamers): 0.56–0.61 (m, 3H), 1.28–1.35 (m, 3H), 1.40–1.76 (m, 4H), 1.95–2.45 (m, 6H), 2.85 (m, 0.56H), 3.10 (m, 0.44H), 3.28–3.90 (m, 6H), 4.30 (m, 0.44H), 4.61 (m, 0.56H), 6.60–6.77 (m, 3H), 7.10 (m, 1H).

Preparation 3

(±)-1-[trans-3,4-Dimethyl-4-(3-hydroxyphenyl) piperidinyl]-3-(tetrahydro-2H-pyran-2-yl)-1-propanone To a solution of 3-(tetrahydropyran-2-yl)propionic acid (prepared as described in Chem. Ber., 1990, 123, 153: 243 mg, 1.54 mmol) in N,N-dimethylformamide (55 mL) at room temperature was added 1-(3-dimethylaminopropyl)-3-ethylcarbodiimide hydrochloride (420 mg, 2.19 mmol) and 1-hydroxybenzotriazole (223 mg, 1.65 mmol). After the mixture had become homogeneous, (±)-3-(trans-3,4-dimethylpiperidinyl)phenol (338 mg, 1.65 mmol) was added in one portion. The mixture was stirred at room temperature for 48 hours and then water (50 mL) was added. The aqueous layer was extracted with diethyl ether (2×150 mL) and the combined organic layers were washed with brine (50 mL), dried over sodium sulfate, filtered and concentrated in vacuo to give a clear residue. This was purified by column chromatography on silica gel, eluting with a gradient of ethyl acetate:hexane (66:44 to 75:25), to give the title compound (473 mg, 90%) as a colourless oil.

$^1$H-NMR (selected data from mixture of rotamers (approximately 1:1)): 0.59–0.68 (m, 3H), 1.38–1.41 (m, 3H), 2.87 (m, 0.5H), 3.15 (m, 0.5H), 3.50–3.70 (m, 1H), 4.35 (m, 0.5H), 4.70 (m, 0.5H), 6.68 (d, 1H), 6.72–6.80 (m, 2H), 7.18 (t, 1H). MS (TSI$^+$): m/z [MH$^+$] 346.3; $C_{21}H_{31}NO_3$+H requires 346.2.

Preparation 4

2-(3-Bromopropyl)-1,3-dioxane

To a solution of 4-bromobutanal (prepared as described in J. Org. Chem., 1979, 44, 3230–3238: 450 mg, 2.98 mmol) in tetrahydrofuran (10 mL) at room temperature was added 1,3-propane diol (1.0 mL, 13.7 mmol) and p-toluenesulfonic acid monohydrate (50 mg, 0.26 mmol). The mixture was heated at reflux for 2 hours, cooled and suspended in a mixture of water and diethyl ether (200 mL of 1:1). The two layers were separated and the organic layer was dried over magnesium sulfate, filtered, and then concentrated in vacuo to give the title compound as a clear oil.

$^1$H-NMR: 1.25–2.20 (m, 6H), 3.43 (t, 2H), 3.75 (m, 2H), 4.10 (dd, 2H), 4.58 (t, 1H).

Preparation 5

(±)-1-[trans-3,4-Dimethyl-4-(3-hydroxyphenyl) piperidinyl]-3-(tetrahydro-2H-pyran-4-yl)-1-propanone To a solution of 3-(tetrahydropyran-4-yl)propionic acid (prepared as described in Justus Leibigs Ann. Chem., 1937, 532, 83: 320 mg, 2.02 mmol) in N,N-dimethylformamide (70 mL) at room temperature was added 1-(3-dimethylaminopropyl)-3-ethylcarbodiimide hydrochloride (552 mg, 2.88 mmol) and 1-hydroxybenzotriazole (293 mg, 2.17 mmol). After the mixture had become homogeneous, (±)-3-(trans-3,4-dimethylpiperidinyl)phenol (338 mg, 1.65 mmol) was added in one portion. The mixture was stirred at room temperature for 16 hours and then water (50 mL) was added. The aqueous layer was extracted with diethyl ether (2×150 mL) and the combined organic layers were washed with brine (50 mL), dried over sodium sulfate, filtered and concentrated in vacuo to give a clear residue. This was purified by column chromatography on silica gel (25 g), eluting with a gradient of ethyl acetate:hexane (66:44 to 75:25), to give the title compound (500 mg, 72%) as a colourless oil.

$^1$H-NMR (selected data from a 4:3 mixture of rotamers): 0.60–0.68 (m, 3H), 1.38–1.40 (m, 3H), 4.38 (m, 0.43H), 4.70 (m, 0.57H), 6.68 (d, 1H), 6.72–6.80 (m, 2H), 7.18 (t, 1H). MS (TSI$^+$): m/z [MH$^+$] 346.1; $C_{21}H_{31}NO_3$+H requires 346.2.

Preparation 6

(±)-1-[trans-3,4-Dimethyl-4-(3-hydroxyphenyl) piperidinyl]-3-(tetrahydro-2-furanyl)-1-propanone To a solution of 3-(tetrahydro-2-furanyl)propionic acid (prepared as described in *J. Amer. Chem. Soc.*, 1923, 45, 3042: 202 mg, 1.40 mmol), in N,N-dimethylformamide (50 mL) at room temperature was added 1-(3-dimethylaminopropyl)-3-ethylcarbodiimide hydrochloride (320 mg, 2.00 mmol) and 1-hydroxybenzotriazole (204 mg, 1.50 mmol). After the mixture become homogeneous, (±)-3-(trans-3,4-dimethylpiperidinyl)phenol (300 mg, 1.50 mmol) was added in one portion. The mixture was stirred at room temperature for 16 hours and then water was added. The aqueous layer was extracted with diethyl ether and the combined organic layers were dried over sodium sulfate, filtered and concentrated in vacuo to give a clear residue. This was purified by column chromatography on silica gel, eluting with a gradient of ethyl acetate:dichloromethane (0:100 to 100:0), to give the title compound (270 mg, 58%) as a colourless gum.

$^1$H-NMR (4:3 mixture of rotamers): 0.58–0.63 (m, 3H), 1.35–1.38 (m, 3H), 1.40–2.60 (m, 11H), 2.82–3.90 (m, 6H), 4.35 (m, 0.43H), 4.68 (m, 0.57H), 6.64 (d, 1H), 6.72–6.78 (m, 2H), 7.15 (t, 1H).

Preparation 7

2-Chloroethyl Ethyl Sulfoxide

To a solution of 3-chloroperoxybenzoic acid (2.95 g, 8.55 mmol) in dichloromethane (25 mL) at 0° C. was added 2-chloroethyl ethyl sulfide (1.0 mL, 8.58 mmol). After 10 minutes at 0° C. the cooling bath was removed and the mixture was stirred at room temperature for 48 hours. The reaction mixture was diluted with dichloromethane (75 mL) and then poured into a saturated aqueous sodium hydrogencarbonate solution (100 mL). The two layers were separated and the aqueous layer was extracted with dichloromethane (2×50 mL). The combined organic layers were dried over sodium sulfate, filtered and concentrated in vacuo to give an oil. This was purified by column chromatography on silica gel (50 g), eluting with ethyl acetate, to give the title compound (740 mg, 61%) as a yellow oil.

$^1$H-NMR: 1.33 (t, 3 H), 2.70–2.81 (m, 2H), 2.92–3.05 (m, 2H), 3.85–3.96 (m, 2H). MS (TSI$^+$): m/z [MNH$_4^+$] 157.9; $C_4H_9ClOS+NH_4$ requires 158.0.

Preparation 8

2-Chloroethyl Ethyl Sulfone

To a solution of 2-chloroethyl ethyl sulfide (1.1 g, 8.58 mmol) in dichloromethane (25 mL) at room temperature was added 3-chloroperoxybenzoic acid (5.9 g, 17.0 mmol) portionwise. The reaction was exothermic and needed to be cooled in an ice bath to complete the addition. A thick white suspension formed and more dichloromethane (25 mL) was added. The mixture was stirred at room temperature for 16 hours and then filtered washing with dichloromethane. The filtrate was washed with a saturated aqueous sodium hydrogencarbonate solution (200 mL). The two layers were separated and the aqueous layer was extracted with dichloromethane (2×100 mL). The combined organic layers were dried over sodium sulfate, filtered and concentrated in vacuo to give a colourless oil. This was purified by column chromatography on silica gel (50 g), eluting with ethyl acetate:hexane (1:3), to give the title compound (1.2 g, 90%) as a colourless oil.

$^1$H-NMR: 1.40 (t, 3 H), 3.08 (q, 2H), 3.35 (t, 2H), 3.90 (t, 2H). MS (TSI$^+$): m/z [MNH$_4^+$] 173.8; $C_4H_9ClO_2S+NH_4$ requires 174.0.

Preparation 9

(1)-1-[trans-3,4-Dimethyl-4-(3-hydroxyphenyl) piperidinyl]-3-(1H-pyrazol-1-yl)-1-propanone To a solution of 3-(pyrazol-1-yl)propionic acid (prepared as described in *Synlett*, 1997, 1013–1034: 225 mg, 1.60 mmol), in N,N-dimethylformamide (50 mL) at room temperature was added 1-(3-dimethylaminopropyl)-3-ethylcarbodiimide hydrochloride (418 mg, 2.18 mmol) and 1-hydroxybenzotriazole (216 mg, 1.60 mmol). After 15 minutes at room temperature the solution was homogeneous and (±)-3-(trans-3,4-dimethylpiperidinyl)phenol (293 mg, 1.43 mmol) was added portionwise. The mixture was stirred at room temperature for 16 hours and then poured into water. The aqueous layer was extracted with diethyl ether (1×20 mL), and then made basic with a 2N aqueous sodium hydroxide solution (to pH 10), and further extracted with diethyl ether. The combined organic layers were washed with brine, dried over magnesium sulfate, filtered and concentrated in vacuo to give the title compound (71 mg, 14%) as an oil. This was used in the next step without further purification.

MS (APCI$^+$): m/z [MH$^+$] 328.0; $C_{19}H_{25}N_3O_2+H$ requires 328.2.

Preparation 10

2-(2-Naphthyloxy)ethyl 4-Bromobenzenesulfonate

To a solution of 2-(2-naphthyloxy)-1-ethanol (1.5 g, 7.97 mmol) and triethylamine (1.21 g, 11.95 mmol) in dichloromethane (20 mL) at 0° C. was added 4-bromobenzenesulfonyl chloride (2.12 g, 8.36 mmol) in dichloromethane (10 mL) dropwise over 30 minutes. The reaction was then warmed to room temperature and stirred for 16 hours before more 4-bromobenzenesulfonyl chloride (0.20 g, 0.80 mmol) was added and stirring was continued for 2 hours. The mixture was then poured into water (50 mL) and acidified with 2N aqueous hydrochloric acid (15 mL). The aqueous layer was extracted with dichloromethane and the combined organic layers were dried over sodium sulfate, filtered and concentrated in vacuo to give a crude residue. This was purified by column chromatography on silica gel (50 g), eluting with hexane:ethyl acetate (9:2), to give the title compound (0.56 g, 17%) as a white crystalline solid.

$^1$H-NMR: 4.25–4.31 (m, 2H), 4.45–4.55 (m, 2H), 6.92–7.02 (m, 2H), 7.36 (t, 1H), 7.45 (t, 1H), 7.62–7.85 (m, 7H). MS (TSI$^+$): m/z [MNH$_4^+$] 424.0; $C_{18}H_{15}BrO_4S+NH_4$ requires 424.0.

Preparation 11

2-(2-Iodoethoxy)naphthalene

To a solution of 2-(2-naphthyloxy)ethyl 4-bromobenzenesulfonate (Preparation 10, 380 mg, 0.93 mmol) in acetone (5 mL) at room temperature was added sodium iodide (1.0 g, 6.66 mmol). The mixture was heated at 35° C. for 16 hours and then cooled. The residual precipitate was removed by filtration and the filtrate was concentrated in vacuo. The residue was partitioned between diethyl ether (20 mL) and water (20 mL). The two layers were separated and the organic layer was dried over sodium sulfate, filtered, and concentrated in vacuo to give the title compound (200 mg, 72%) as a pale yellow oil.

$^1$H-NMR: 3.50 (t, 2H), 4.39 (t, 2H), 7.10–7.20 (m, 2H), 7.30–7.50 (m, 2H), 7.65–7.84 (m, 3H).

Preparation 12

2-Isopropoxyethyl 4-Bromobenzenesulfonate

To a solution of 2-isopropoxy-1-ethanol (1.5 g, 14.4 mmol) and triethylamine (2.2 g, 21.6 mmol) in dichloromethane (20 mL) at 0° C. was added 4-bromobenzenesulfonyl chloride (2.12 g, 8.36 mmol) in dichloromethane (10 mL) dropwise over 30 minutes. The reaction was then warmed to room temperature and stirred for 16 hours. The mixture was then poured into water (50 mL) and acidified with 2N aqueous hydrochloric acid (15 mL). The aqueous layer was extracted with dichloromethane and the combined organic layers were dried over sodium sulfate, filtered and concentrated in vacuo to give a crude residue. This was purified by column chromatography on silica gel (50 g), eluting with hexane:ethyl acetate (9:3), to give the title compound (4.0 g, 86%) as a colourless oil.

$^1$H-NMR: 1.08 (d, 6H), 3.52 (m, 1H), 3.60 (t, 2H), 4.19 (t, 2H), 7.70 (d, 2H), 7.80 (d, 2H).

Preparation 13

2-(2-Iodoethoxy)propane

To a solution of 2-isopropoxyethyl 4-bromobenzenesulfonate (Preparation 12, 1.0 g, 3.08 mmol) in acetone (5 mL) at room temperature was added sodium iodide (1.0 g, 6.66 mmol). The mixture was heated at 35° C. for 16 hours and then cooled. The residual precipitate was removed by filtration and the filtrate was concentrated in vacuo. The residue was partitioned between diethyl ether (20 mL) and water (20 mL). The two layers were separated and the organic layer was dried over sodium sulfate, filtered, and concentrated in vacuo to give the title compound (180 mg, 27%) as a pale brown oil.

$^1$H-NMR: 1.19 (d, 6H), 3.22 (t, 2H), 3.60–3.72 (m, 3H).

Preparation 14

2-Propoxyethyl 4-Bromobenzenesulfonate

To a solution of 2-propoxy-1-ethanol (1.5 g, 14.4 mmol) and triethylamine (2.2 g, 21.6 mmol) in dichloromethane (20 mL) at 0° C. was added 4-bromobenzenesulfonyl chloride (3.86 g, 15.1 mmol) in dichloromethane (10 mL) dropwise over 30 minutes. The reaction was then warmed to room temperature and stirred for 16 hours. The mixture was then poured into water (50 mL) and acidified with 2N aqueous hydrochloric acid (15 mL). The aqueous layer was extracted with dichloromethane and the combined organic layers were dried over sodium sulfate, filtered and concentrated in vacuo to give a crude residue. This was purified by column chromatography on silica gel (50 g), eluting with hexane-:ethyl acetate (9:3), to give the title compound (2.2 g, 48%) as a colourless oil.

$^1$H-NMR: 0.86 (t, 3H), 1.52 (m, 2H), 3.36 (t, 2H), 3.62 (t, 2H), 4.21 (t, 2H), 7.70 (d, 2H), 7.80 (d, 2H). MS (TSI$^+$): m/z [MNH$_4^+$] 323.0; C$_{11}$H$_{15}$BrO$_4$S+H requires 323.0.

Preparation 15

1-(2-Iodoethoxy)propane

To a solution of 2-propoxyethyl 4-bromobenzenesulfonate (Preparation 14, 1.0 g, 3.08 mmol) in acetone (5 mL) at room temperature was added sodium iodide (1.0 g, 6.66 mmol). The mixture was heated at 35° C. for 16 hours and then cooled. The residual precipitate was removed by filtration and the filtrate was concentrated in vacuo. The residue was partitioned between diethyl ether (20 mL) and water (20 mL). The two layers were separated and the organic layer was dried over sodium sulfate, filtered, and concentrated in vacuo to give the title compound (400 mg, 61%) as a pale yellow oil.

$^1$H-NMR: 0.92 (t, 3H), 1.60 (m, 2H), 3.24 (t, 2H), 3.42 (t, 2H), 3.70 (t, 2H).

Preparation 16

2-(Cyclopentyloxy)ethyl 4-Bromobenzenesulfonate

To a solution of 2-(cyclopentyloxy)-1-ethanol (prepared as described in J. Org. Chem., 1968, 33, 2271–2284: 127 mg, 0.97 mmol) and triethylamine (101 mg, 0.1 mmol) in dichloromethane (3 mL) at 0° C. was added 4-bromobenzenesulfonyl chloride (255 mg, 0.1 mmol) in dichloromethane (2 mL) dropwise over 5 minutes. The reaction was then warmed to room temperature and stirred for 16 hours. The mixture was then poured into water (3 mL) and the two layers were separated. The organic layer was dried over sodium sulfate, filtered and concentrated in vacuo to give a crude residue. This was purified by column chromatography on silica gel (50 g), eluting with a gradient of dichloromethane:hexane (50:50 to 0:100), to give the title compound (200 mg, 59%) as a colourless oil.

$^1$H-NMR: 1.40–1.78 (m, 8H), 3.57 (t, 2H), 3.80–3.90 (m, 1H), 4.20 (t, 2H), 7.67 (d, 2H), 7.78 (d, 2H). MS (TSI$^+$): m/z [MNH$_4^+$] 366.0; C$_{13}$H$_{21}$BrO$_4$S+NH$_4$ requires 366.0.

Preparation 17

1-(2-Iodoethoxy)cyclopentane

To a solution of 2-(cyclopentyloxy)ethyl 4-bromobenzenesulfonate (Preparation 16, 60 mg, 0.17 mmol) in acetone (5 mL) at room temperature was added sodium iodide (200 mg, 1.3 mmol). The mixture was,heated at 35° C. for 16 hours and then cooled. The residual precipitate was removed by filtration and the filtrate was concentrated in vacuo. The residue was partitioned between diethyl ether (10 mL) and water (10 mL). The two layers were separated and the organic layer was dried over sodium sulfate, filtered, and concentrated in vacuo to give the title compound (15 mg, 37%) as a brown oil.

$^1$H-NMR: 1.42–1.80 (m, 8H), 3.22 (t, 2H), 3.67 (t, 2H), 3.93–4.01 (m, 1H).

Preparation 18

2-(Cyclohexyloxy)ethyl-4-methylbenzenesulfonate

To a solution of 2-(cyclohexyloxy)-1-ethanol (200 mg, 1.39 mmol) in pyridine (10 mL) at 0° C. was added p-toluenesulfonyl chloride (292 mg, 1.53 mmol) portionwise followed by 4-(dimethylamino)pyridine (a few crystals) and the mixture was stirred at room temperature for 16 hours. The solvent was removed in vacuo to give a crude residue that was partitioned between dichloromethane and 2N aqueous hydrochloric acid. The two layers were separated and the organic layer was dried over sodium sulfate, filtered and concentrated in vacuo to give a yellow oil. This was purified by column chromatography on silica gel, eluting with dichloromethane, to give the title compound (226 mg, 54%) as a yellow oil.

MS (TSI⁺): m/z [MH⁺] 299.3; $C_{15}H_{22}SO_4+H$ requires 299.1.

What is claimed is:

1. A compound of formula I,

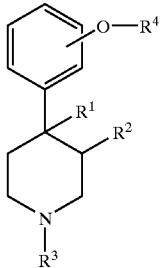

wherein $R^1$ and $R^2$ are each independently H or $C_{1-4}$ alkyl;

$R^3$ represents phenyl (optionally substituted by one or more substituents selected from the group consisting of OH, nitro, halo, CN, $CH_2CN$, $CONH_2$, $C_{1-4}$ alkyl, $C_{1-5}$ alkanoyl (which latter three groups are optionally substituted by one or more halo atoms) and $-N(R^{5a})(R^{5b})$);

$R^{5a}$ and $R^{5b}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

Het represents a 3- to 8-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms); and $R^4$ represents H, $C_{1-5}$ alkyl, or $C_{1-2}$ alkanoyl;

or a pharmaceutically, or a veterinarily, acceptable derivative thereof, said $OR^4$ group is attached to the benzene ring in the meta position relative to the piperidine group.

2. A compound as claimed in claim 1, wherein $R^1$ represents $C_{1-2}$ alkyl.

3. A compound as claimed in claim 1, wherein $R^2$ represents H or $C_{1-2}$ alkyl.

4. A compound as claimed in claim 1, wherein $R^3$ represents phenyl (optionally substituted by one or more substituents selected from $C_{1-2}$ alkyl, $C_{1-2}$ alkoxy, halo, nitro and $-N(R^{5a})(R^{5b})$).

5. A compound as claimed in claim 1, wherein $R^{5a}$ and $R^{5b}$ each independently represent H, $C_{1-6}$ alkyl, $C_{3-6}$ alkenyl, $C_{3-6}$ alkynyl, $C_{4-8}$ cycloalkyl, $C_{1-2}$ alkylphenyl, aryl or $Het^2$.

6. A compound as claimed in claim 1, wherein $Het^2$ represents a 5- to 7-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substituents selected from OH, =O and $C_{1-2}$ alkyl (which latter group is optionally substituted by one or more halo atoms).

7. A compound as claimed in claim 1, wherein $R^4$ represents H or $C_{1-5}$ alkanoyl.

8. A pharmaceutical composition comprising a therapeutically effective amount of compound of Formula I,

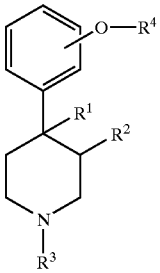

or a pharmaceutically or a veterinarily, acceptable derivative thereof, in a pharmaceutically acceptable amount, in admixture with a pharmaceutically or veterinarily, acceptable adjuvant, diluent, or carrier, wherein $R^1$ and $R^2$ are each independently H or $C_{1-4}$ alkyl;

$R^3$ represents phenyl (optionally substituted by one or more substituents selected from the group consisting of OH, nitro, halo, CN, $CH_2CN$, $CONH_2$, $C_{1-4}$ alkyl, $C_{1-5}$ alkanoyl (which latter three groups are optionally substituted by one or more halo atoms) and $-N(R^{5a})(R^{5b})$);

$R^{5a}$ and $R^{5b}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

$Het^2$ represents a 3- to 8-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substuents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms); and $R^4$ represents H, $C_{1-5}$ alkyl, or $C_{1-12}$ alkanoyl.

9. A pharmaceutical composition as claimed in claim 8, which is a veterinary pharmaceutical composition.

10. A method of treating pruritus, which comprises administering to a patient in need of such treatment a therapeutically effective amount of a compound of Formula I

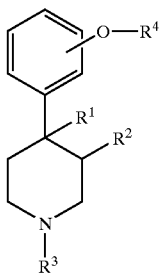

wherein $R^1$ and $R^2$ are each independently H or $C_{1-4}$ alkyl;

$R^3$ represents phenyl (optionally substituted by one or more substituents selected from the group consisting of OH, nitro, halo, CN, $CH_2CN$, $CONH_2$, $C_{1-4}$ alkyl, $C_{1-5}$ alkanoyl (which latter three groups are optionally substituted by one or more halo atoms) and —N($R^{5a}$)($R^{5b}$));

$R^{5a}$ and $R^{5b}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by one or more substituents selected from the group consisting of OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$;

$Het^2$ represents 3- to 8-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substituents selected from the group consisting of OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms); and $R^4$ represents H, $C_{1-5}$ alkyl, or $C_{1-12}$ alkanoyl;

or a pharmaceutically, or veterinarily, acceptable derivative thereof.

11. A process for the preparation of a compound of formula I

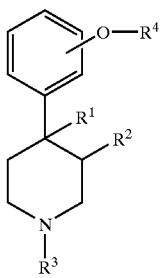

in which $R^4$ represents $C_{1-12}$ alkanoyl;

$R^1$ and $R^2$ are each independently H or $C_{1-4}$ alkyl;

$R^3$ represents phenyl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —N($R^{5a}$)($R^{5b}$));

$R^{5a}$ and $R^{5b}$ each independently represent H, $C_{110}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, $CH_2CN$, $CONH_2$, $C_{1-4}$ alkyl, $C_{1-4}$ alkoxy and $C_{1-5}$ alkanoyl (which latter three groups are optionally substituted by one or more halo atoms)) or $Het^2$; and $Het^2$ represents a 3- to 8-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substituents selected from OH, =O, nitro, amino, halo, CN, aryl, $C_{1-4}$ alkyl, $C_{1-4}$ alkoxy and $C_{1-5}$ alkanoyl (which latter three groups are optionally substituted by one or more halo atoms);

which process comprises reaction of a corresponding compound of said compound of formula I but in which $R^4$ represents H with a compound of formula V, $$R^{41}\text{—}CO_2H \qquad\qquad V$$

or a suitable derivative thereof, wherein $R^{41}$ represents $C_{1-11}$ alkyl.

12. A process for a preparation of a compound of formula I

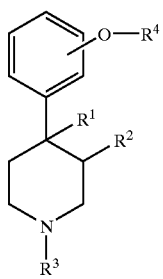

in which $R^1$ and $R^2$ are each independently H or $C_{1-4}$ alkyl;

$R^3$ represents phenyl (optionally substituted by one or more substituents selected from OH, nitro, halo, CN, $CH_2CN$, $CONH_2$, $C_{1-4}$ alkyl, $C_{1-4}$ alkoxy, $C_{1-5}$ alkanoyl (which latter three groups are optionally substituted by one or more halo atoms) and —N($R^{5a}$)($R^{5b}$));

$R^4$ represents H, $C_{1-5}$ alkyl, $C_{1-12}$ alkanoyl;

$R^{5a}$ and $R^{5b}$ each independently represent H, $C_{1-10}$ alkyl, $C_{3-10}$ alkenyl, $C_{3-10}$ alkynyl, $C_{3-8}$ cycloalkyl, $C_{1-4}$ alkylphenyl, aryl (which latter six groups are optionally substituted by or one or more substituents selected from OH, nitro, amino, halo, CN, CH$_2$CN, CONH$_2$, C$_{1-4}$ alkyl, C$_{1-4}$ alkoxy and C$_{1-5}$ alkanoyl (which latter three groups are optionally substituted by one or more halo atoms)) or Het$^2$; and Het$^2$ represents a 3- to 8-membered heterocyclic group, which group contains at least one heteroatom selected from oxygen, sulfur and/or nitrogen, which group is optionally fused to a benzene ring, and which group is optionally substituted in the heterocyclic and/or fused benzene ring part by one or more substituents selected from OH, =O, nitro, amino, halo, CN, aryl, C$_{1-4}$ alkyl, C$_{1-4}$ alkoxy and C$_{1-5}$ alkanoyl (which latter three groups are optionally substituted by one or more halo atoms);

which process comprises reaction of a compound of formula III

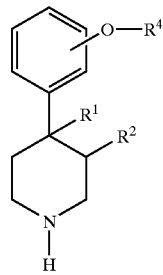

III with a compound of formula VI,

R$^3$—L$^1$   VI wherein L$^1$ represents a leaving group.

* * * * *